US012596112B2

(12) United States Patent
Kakimoto et al.

(10) Patent No.: US 12,596,112 B2
(45) Date of Patent: Apr. 7, 2026

(54) EDIBLE OIL DETERIORATION LEVEL DETERMINATION DEVICE, EDIBLE OIL DETERIORATION LEVEL DETERMINATION SYSTEM, EDIBLE OIL DETERIORATION LEVEL DETERMINATION METHOD, EDIBLE OIL DETERIORATION LEVEL DETERMINATION PROGRAM, EDIBLE OIL DETERIORATION LEVEL LEARNING DEVICE, LEARNED MODEL FOR USE IN EDIBLE OIL DETERIORATION LEVEL DETERMINATION, AND EDIBLE OIL EXCHANGE SYSTEM

(71) Applicant: J-Oil Mills, Inc., Tokyo (JP)

(72) Inventors: Kenichi Kakimoto, Tokyo (JP); Ryohei Watanabe, Tokyo (JP); Masami Inoue, Tokyo (JP)

(73) Assignee: J-OIL MILLS, Inc., Tokyo (JP)

( * ) Notice: Subject to any disclaimer, the term of this patent is extended or adjusted under 35 U.S.C. 154(b) by 774 days.

(21) Appl. No.: 17/914,812

(22) PCT Filed: Mar. 16, 2021

(86) PCT No.: PCT/JP2021/010542
§ 371 (c)(1),
(2) Date: Sep. 27, 2022

(87) PCT Pub. No.: WO2021/200103
PCT Pub. Date: Oct. 7, 2021

(65) Prior Publication Data
US 2023/0140684 A1     May 4, 2023

(30) Foreign Application Priority Data
Mar. 31, 2020     (JP) ................................. 2020-063557

(51) Int. Cl.
*G01N 33/03*         (2006.01)

(52) U.S. Cl.
CPC .................................... *G01N 33/03* (2013.01)

(58) Field of Classification Search
None
See application file for complete search history.

(56) References Cited

U.S. PATENT DOCUMENTS 6,274,850 B1     8/2001   Mercer
2011/0129578 A1*  6/2011   Feinberg ............. A47J 37/1266
                                                              426/233

(Continued)

FOREIGN PATENT DOCUMENTS

JP           H07151722       6/1995
JP           H08182624       7/1996

(Continued)

OTHER PUBLICATIONS

International Search Report and Written Opinion dated Jun. 8, 2021; PCT/JP2021/010542; 5 pages.

*Primary Examiner* — Daniel S Larkin
(74) *Attorney, Agent, or Firm* — RANKIN, HILL & CLARK LLP; Erik J. Overberger

(57)                    ABSTRACT

Provided is an edible oil deterioration level determination device and the like capable of precisely determining the deterioration level of frying oil. A deterioration level determination device 5 for determining the deterioration level of frying oil Y comprises an air bubble image extraction section 51 for extracting an air bubble image that is an image of a portion of air bubbles formed due to deep-fry cooking from an oil surface image, a feature parameter calculation section 54 for calculating a feature parameter F characterizing deterioration of the frying oil Y from the air bubble image extracted by the air bubble image extraction section 51, a deterioration indicator estimation section 55 for estimating a deterioration indicator DI of the frying oil Y based on the feature parameter F, and a deterioration level determination (Continued)

section 56 for determining the deterioration level of the frying oil Y based on the deterioration indicator DI.

11 Claims, 20 Drawing Sheets

(56)                    References Cited

U.S. PATENT DOCUMENTS

2019/0041375  A1*    2/2019   Yamasaki  .............. G01N 33/03
2022/0061590  A1*    3/2022   Iassonova  ................ A23L 5/11

FOREIGN PATENT DOCUMENTS

JP           2004008255       1/2004
JP           2006226735       8/2006
JP           2016085117       5/2016

* cited by examiner

CORRELATION BETWEEN AREA RATIO OF
ALL AIR BUBBLES AND COLOR

CORRELATION BETWEEN AREA RATIO OF
LARGE AIR BUBBLES AND COLOR

CORRELATION BETWEEN AREA RATIO OF
FINE AIR BUBBLES AND COLOR

CORRELATION BETWEEN AREA RATIO OF
ALL AIR BUBBLES AND ACID VALUE

CORRELATION BETWEEN AREA RATIO OF
LARGE AIR BUBBLES AND ACID VALUE

CORRELATION BETWEEN AREA RATIO OF
FINE AIR BUBBLES AND ACID VALUE

CORRELATION BETWEEN AREA RATIO OF
ALL AIR BUBBLES AND INCREASE RATE OF VISCOSITY

CORRELATION BETWEEN AREA RATIO OF
LARGE AIR BUBBLES AND INCREASE RATE OF VISCOSITY

CORRELATION BETWEEN AREA RATIO OF
FINE AIR BUBBLES AND INCREASE RATE OF VISCOSITY

FIG. 6A
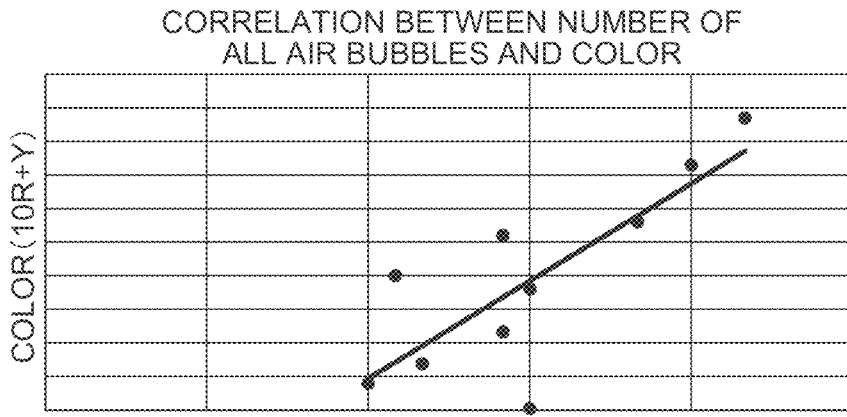
CORRELATION BETWEEN NUMBER OF
ALL AIR BUBBLES AND COLOR
COLOR(10R+Y)
NUMBER OF ALL AIR BUBBLES
FIG. 6B
CORRELATION BETWEEN NUMBER OF
LARGE AIR BUBBLES AND COLOR
COLOR(10R+Y)
NUMBER OF LARGE AIR BUBBLES
FIG. 6C
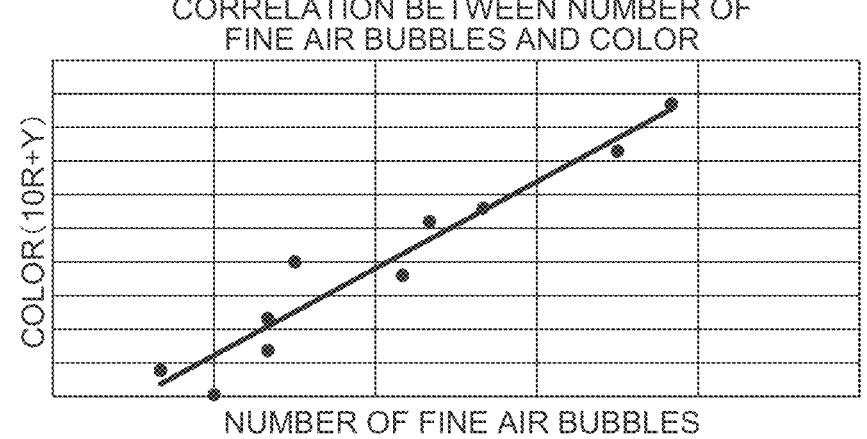
CORRELATION BETWEEN NUMBER OF
FINE AIR BUBBLES AND COLOR
COLOR(10R+Y)
NUMBER OF FINE AIR BUBBLES

CORRELATION BETWEEN NUMBER OF
ALL AIR BUBBLES AND ACID VALUE

CORRELATION BETWEEN NUMBER OF
LARGE AIR BUBBLES AND ACID VALUE

CORRELATION BETWEEN NUMBER OF
FINE AIR BUBBLES

CORRELATION BETWEEN NUMBER OF
ALL AIR BUBBLES AND INCREASE RATE OF VISCOSITY

CORRELATION BETWEEN NUMBER OF
LARGE AIR BUBBLES AND INCREASE RATE OF VISCOSITY

CORRELATION BETWEEN NUMBER OF
FINE AIR BUBBLES AND INCREASE RATE OF VISCOSITY

FIG. 9

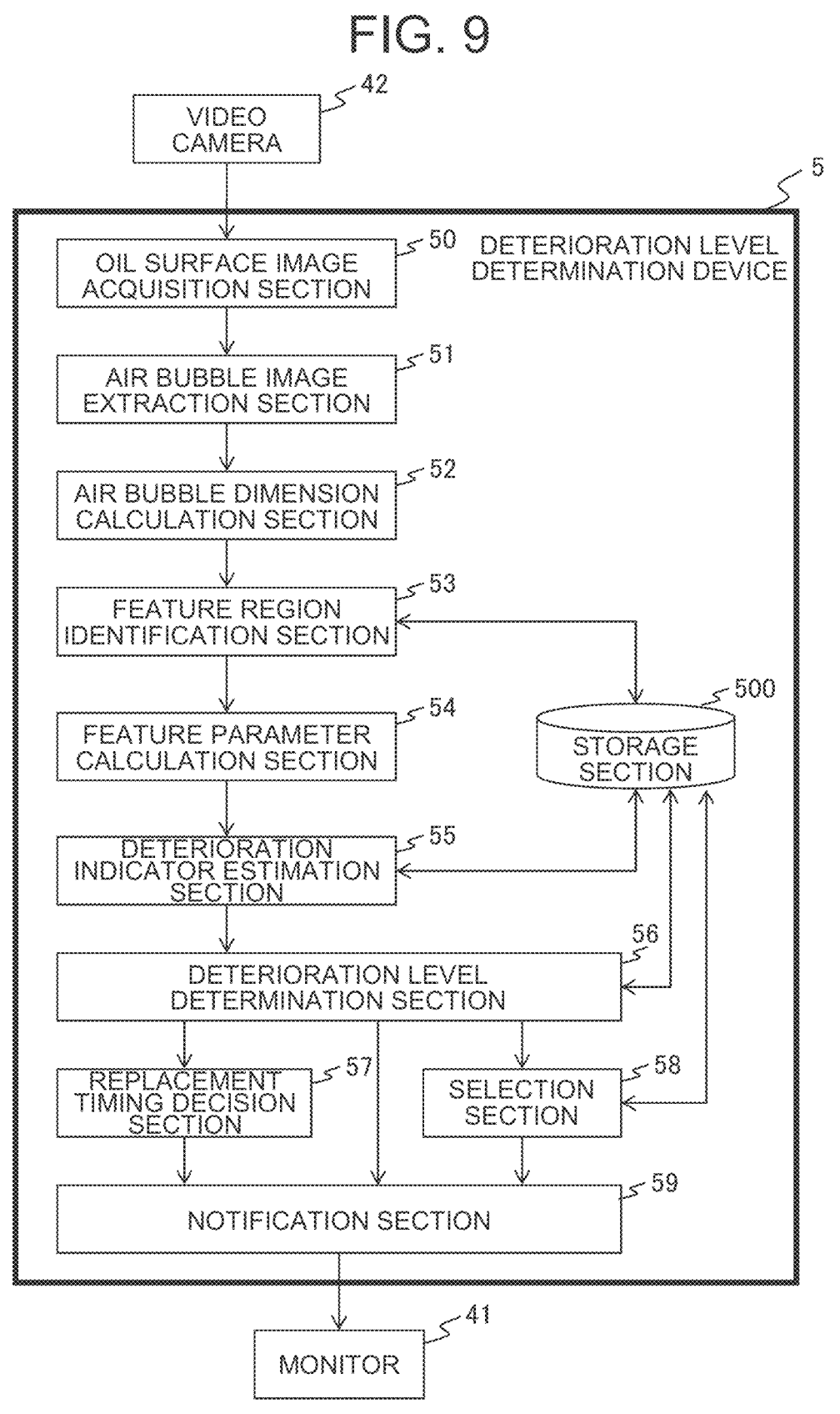

VIDEO CAMERA — 42

— 5

DETERIORATION LEVEL DETERMINATION DEVICE

OIL SURFACE IMAGE ACQUISITION SECTION — 50

AIR BUBBLE IMAGE EXTRACTION SECTION — 51

AIR BUBBLE DIMENSION CALCULATION SECTION — 52

FEATURE REGION IDENTIFICATION SECTION — 53

FEATURE PARAMETER CALCULATION SECTION — 54

STORAGE SECTION — 500

DETERIORATION INDICATOR ESTIMATION SECTION — 55

DETERIORATION LEVEL DETERMINATION SECTION — 56

REPLACEMENT TIMING DECISION SECTION — 57

SELECTION SECTION — 58

NOTIFICATION SECTION — 59

MONITOR — 41

CORRELATION BETWEEN NUMBER OF
AIR BUBBLES AND COLOR

CORRELATION BETWEEN NUMBER OF
AIR BUBBLES AND ACID VALUE

CORRELATION BETWEEN NUMBER OF
AIR BUBBLES AND INCREASE RATE OF VISCOSITY

CORRELATION BETWEEN DISAPPEARANCE SPEED
AND COLOR

CORRELATION BETWEEN DISAPPEARANCE SPEED
AND ACID VALUE

CORRELATION BETWEEN DISAPPEARANCE SPEED
AND INCREASE RATE OF VISCOSITY

FIG. 14A
CORRELATION BETWEEN CONTOUR OF
DEEP-FRIED FOOD AND COLOR
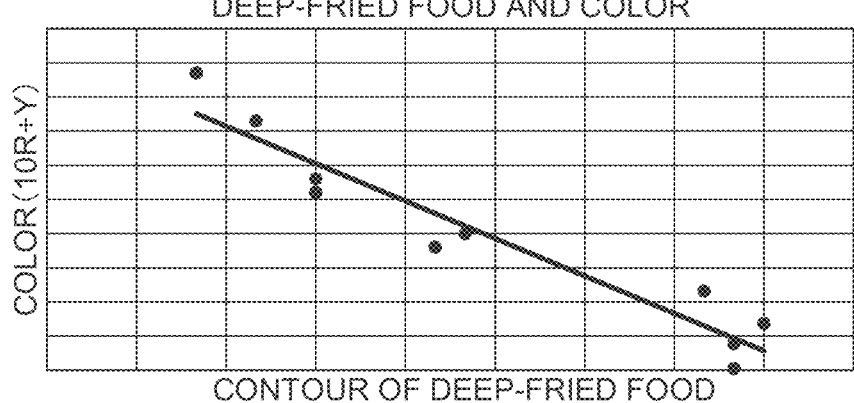
FIG. 14B
CORRELATION BETWEEN CONTOUR OF
DEEP-FRIED FOOD AND ACID VALUE
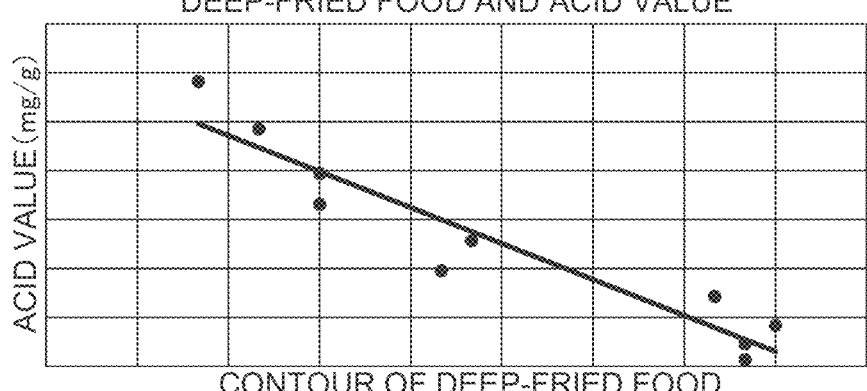
FIG. 14C
CORRELATION BETWEEN CONTOUR OF
DEEP-FRIED FOOD AND INCREASE RATE OF VISCOSITY

CORRELATION BETWEEN PREDICTED VALUE
AND MEASURED VALUE OF ACID VALUE

MEASURED VALUE

PREDICTED VALUE

FIG. 19
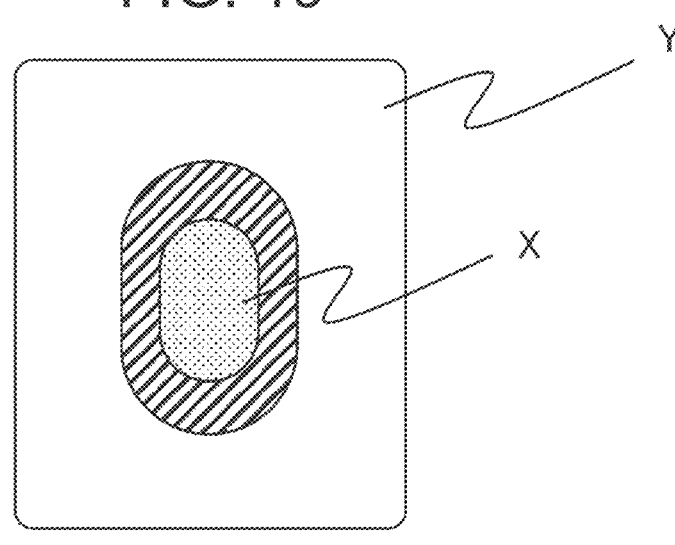
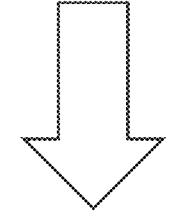
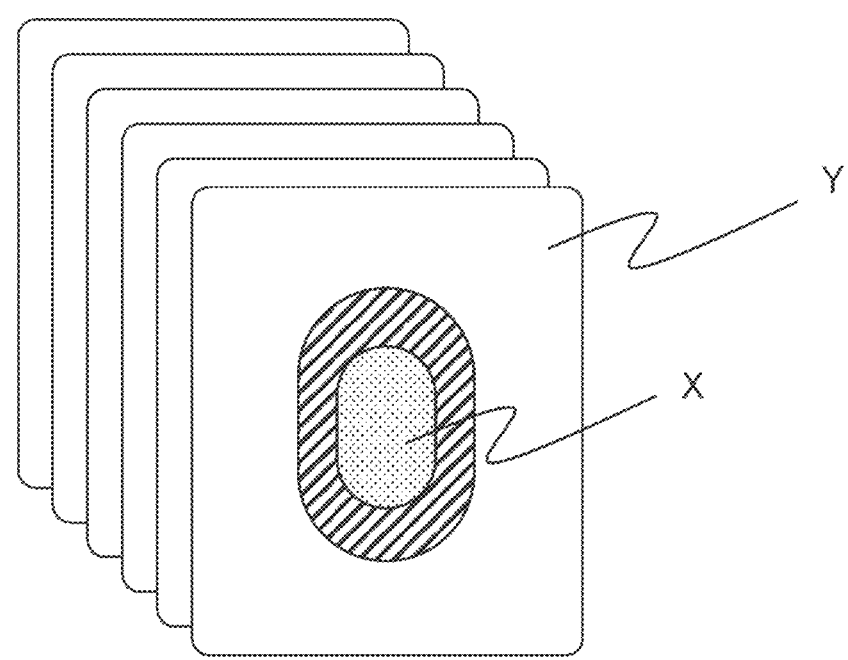

CORRELATION BETWEEN CUMULATIVE VALUE OF
AREA OF AIR BUBBLES AND COLOR

CUMULATIVE VALUE OF AREA OF AIR BUBBLES

CORRELATION BETWEEN CUMULATIVE VALUE OF
AREA OF AIR BUBBLES AND ACID VALUE

CUMULATIVE VALUE OF AREA OF AIR BUBBLES

CORRELATION BETWEEN CUMULATIVE VALUE OF
AREA OF AIR BUBBLES AND VISCOSITY

CUMULATIVE VALUE OF AREA OF AIR BUBBLES

EDIBLE OIL DETERIORATION LEVEL DETERMINATION DEVICE, EDIBLE OIL DETERIORATION LEVEL DETERMINATION SYSTEM, EDIBLE OIL DETERIORATION LEVEL DETERMINATION METHOD, EDIBLE OIL DETERIORATION LEVEL DETERMINATION PROGRAM, EDIBLE OIL DETERIORATION LEVEL LEARNING DEVICE, LEARNED MODEL FOR USE IN EDIBLE OIL DETERIORATION LEVEL DETERMINATION, AND EDIBLE OIL EXCHANGE SYSTEM

TECHNICAL FIELD

The present invention relates to a deterioration level determination device for determining the level of deterioration of edible oil, a deterioration level determination system, a deterioration level determination method, an edible oil deterioration level determination program, an edible oil deterioration level learning device, a learned model for use in the edible oil deterioration level determination, and an edible oil replacement system.

BACKGROUND ART

In order to maintain the quality of deep-fried foods, it is necessary to appropriately manage the edible oil (hereinafter, referred to as "frying oil") used for cooking the deep-fried foods (hereinafter, referred to as "deep-fry cooking"). Conventionally, there has been known a method of determining the level of deterioration of frying oil (hereinafter referred to as "deterioration level") by referring to variation in the appearance, odor, color tone, and the like of the frying oil and a cumulative time (cumulative period of time) in which the frying oil has been used, in order to objectively determine when to change the frying oil.

However, the conventional method of determining the deterioration level often depends on the experience (subjectivity) of a person who is in charge of determination (in many cases, such a person is a user of the frying oil). Therefore, as a method for objectively determining the deterioration level of frying oil without depending on the subjectivity, for example, Patent Literature 1 discloses a method of detecting the deterioration level of the quality of frying oil by using, as an indicator, variation in the illuminance of a surface of the frying oil during deep-fry cooking.

CITATION LIST

Patent Literature

Patent Literature 1: JP-A-H08-182624

SUMMARY OF INVENTION

Technical Problem

According to the method for detecting the deterioration level of frying oil disclosed in Patent Literature 1, the deterioration level of the frying oil can be estimated based on the degree of formation of air bubbles (surface air bubbles) which rise to the surface of frying oil during deep-fry cooking. Among the surface air bubbles, some air bubbles are more likely to appear as the frying oil deteriorates. The degree of formation (quantity, frequency, etc.) of air bubbles that are more likely to appear as the frying oil deteriorates correlates more strongly with the deterioration level of the frying oil. However, since the detection according to the method described in Patent Literature 1 is merely based on the illuminance of the surface of the frying oil, it is difficult to distinguish the types of the surface air bubbles of the frying oil and the frequencies of formation thereof. Accordingly, it has not been able to determine the deterioration level of frying oil which has been deteriorated considering the type of the air bubbles which appear on the surface thereof.

Therefore, an object of the present invention is to provide an edible oil deterioration level determination device capable of determining the deterioration level of frying oil, an edible oil deterioration level determination system, an edible oil deterioration level determination method, an edible oil deterioration level determination program, an edible oil deterioration level learning device, a learned model for use in the edible oil deterioration level determination, and an edible oil replacement system.

Solution to Problem

In order to achieve the object described above, the present invention provides an edible oil deterioration level determination device for determining a deterioration level of edible oil used for deep-fry cooking performed to cook a deep-fried food, the edible oil deterioration level determination device comprising: an air bubble image extraction section configured to extract an air bubble image, which is an image of a portion of air bubbles formed due to the deep-fry cooking, from an oil surface image which is an image of a surface of the edible oil during the deep-fry cooking; a feature parameter calculation section configured to calculate a feature parameter, which is a parameter characterizing deterioration of the edible oil, from the air bubble image extracted by the air bubble image extraction section; a deterioration indicator estimation section configured to estimate a deterioration indicator of the edible oil based on the feature parameter calculated by the feature parameter calculation section; and a deterioration level determination section configured to determine the deterioration level of the edible oil based on the deterioration indicator estimated by the deterioration indicator estimation section.

Advantageous Effects of Invention

According to the present invention, it is possible to determine the level of deterioration of frying oil with high precision. The problems, configurations, and advantageous effects other than those described above will be clarified by explanation of the embodiments below.

BRIEF DESCRIPTION OF DRAWINGS

FIG. 6A is a graph illustrating a correlation between the number of all air bubbles formed on a surface of frying oil and the color tone.

FIG. 6B is a graph illustrating a correlation between the number of large air bubbles among air bubbles formed on a surface of frying oil and the color tone.

FIG. 6C is a graph illustrating a correlation between the number of fine air bubbles among air bubbles formed on a surface of frying oil and the color tone.

FIG. 9 is a functional block diagram illustrating functions of a deterioration level determination device.

FIG. 14A is a graph illustrating a correlation between the visibility level of the contour of a deep-fried food and the color tone.

FIG. 14B is a graph illustrating a correlation between the visibility level of the contour of a deep-fried food and the acid value.

FIG. 14C is a graph illustrating a correlation between the visibility level of the contour of a deep-fried food and the increase rate of viscosity.

FIG. 19 is a diagram for explaining a method of calculating a cumulative value of the area of air bubbles in a deterioration level determination device.

DESCRIPTION OF EMBODIMENTS

An edible oil deterioration level determination system according to each embodiment of the present invention is a system for determining the deterioration level of edible oil used for cooking of deep-fried foods such as fried chickens, deep-fried mashed potatoes, French fries, and the like. In the following, cooking of deep-fried foods is referred to as "deep-fry cooking" and cooking oil used for deep-fry cooking is referred to as "frying oil".

(Arrangement in Cooking Area 1)

Firstly, an example of arrangement in a cooking area 1, which is assumed as an environment in which deep-fry cooking is performed, will be described with reference to FIG. 1.

Figure 1:
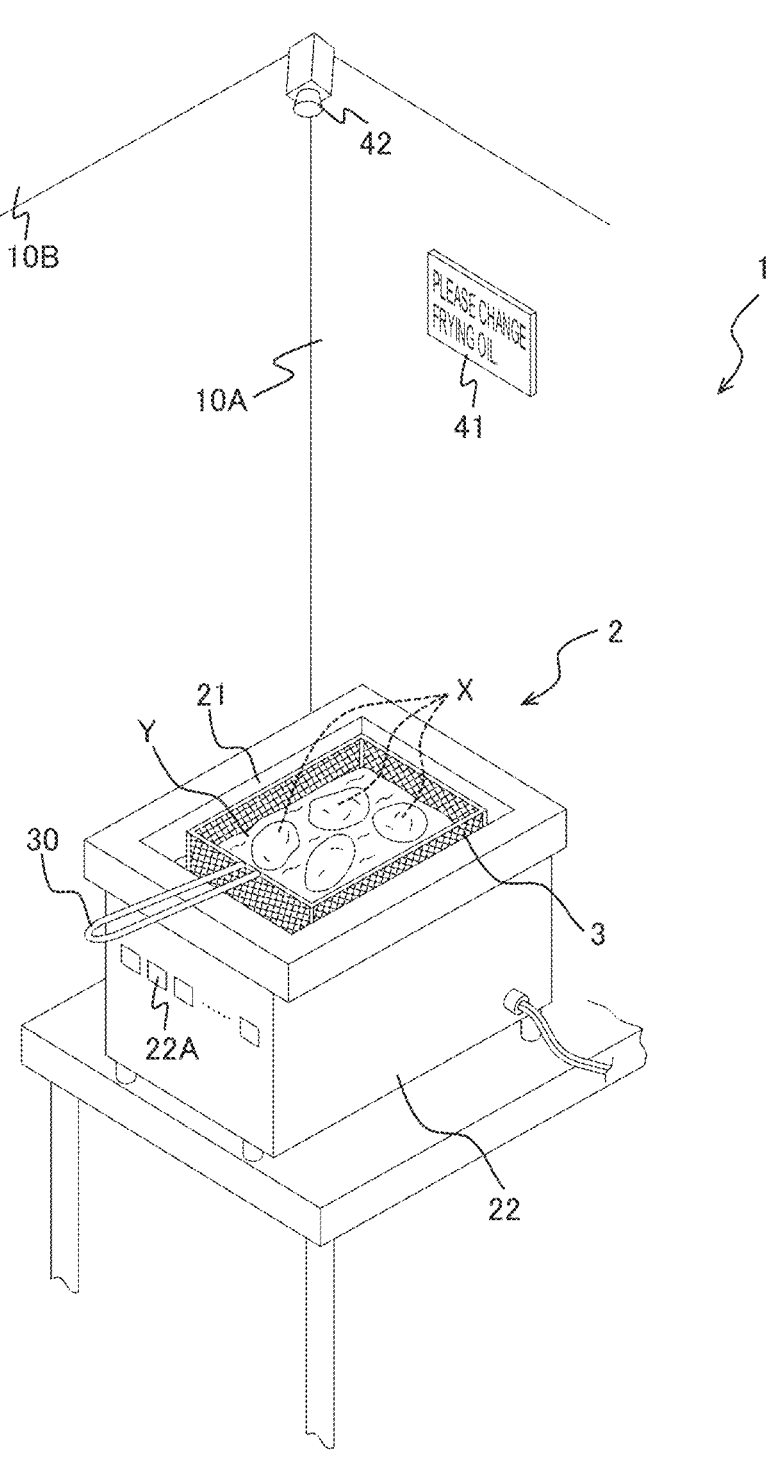
FIG. 1 illustrates an example of arrangement in a cooking area where deep-fry cooking is performed.

FIG. 1 illustrates an example of the arrangement in the cooking area 1 where deep-fry cooking is performed.

The cooking area 1 is built in stores and shops such as a convenience store or a supermarket. The cooking area 1 is provided with a tool in which deep-fry cooking is performed so as to produce a deep-fried food X to be sold to customers, which is, for example, an electric fryer 2. The fryer 2 includes an oil vat 21 for holding frying oil Y therein, and a housing 22 for accommodating the oil vat 21. On a side surface of the housing 22, a plurality of switches 22A serving as a setting operation unit for setting the temperature of the frying oil Y and the details of the deep-fry cooking is provided for each type of the deep-fried food X.

In order to deep-fry the foods, firstly, a cook places the deep-fried food X before deep-fried in a fry basket 3 having a handle 30, and then hooks the handle 30 on the upper end portion of the housing 22 so that the deep-fried food X before deep-fried in the fry basket 3 is immersed in the frying oil Y. At the same time or around the same time, the cook presses one of the switches 22A which corresponds to the type of the deep-fried food X in cooking.

Subsequently, the fryer 2 identifies the one of the switches 22A which was manipulated by the cook, and when a period of time for completion of deep-fry cooking, which is associated with the manipulated one of the switches 22A, elapses, the fryer 2 notifies the cook of the completion of frying. At the same time, the fry basket 3 holding the deep-fried food X automatically rises from the oil vat 21 so that the deep-fried food X is pulled up from the state of being immersed in the frying oil. As a method of informing the completion of deep-fry cooking of the deep-fried food X, for example, a method of outputting a buzzer sound from a speaker of the fryer 2 or a method of displaying the information on a monitor 41 installed on a wall 10A near the fryer 2 may be employed. That is, each of the speaker and the monitor 41 is one of the aspects of a notification device.

The cook who is aware of the completion of deep-fry cooking of the deep-fried food X pulls up the fry basket 3 to take the deep-fried food X out therefrom. Note that pulling up the fry basket 3 out from the oil vat 21 may be automatically performed by a drive mechanism which can be provided in the fryer 2.

In the cooking area 1, a video camera 42 serving as an imaging device for acquiring an oil surface image which is an image of the surface of the frying oil Y in the oil vat 21 is attached to a ceiling 10B above the oil vat 21. The video camera 42 is installed with its angle of view and focus being adjusted so that an image of the surface of the frying oil Y in the oil vat 21 can be continuously captured as an image of the surface of the frying oil Y in the oil vat 21.

Note that the video camera 42 does not necessarily have to be attached to the ceiling 10B. The video camera 42 may be attached to, for example, the wall 10A as long as it is held at a position allowing the oil surface image to be captured. Furthermore, the imaging device does not necessarily have to be the video camera 42 for capturing a moving image, but may be, for example, a still camera for capturing a still image. In the case of using a still camera, it may be configured to automatically capture an oil surface image intermittently.

(Correlation Between Deterioration of Frying Oil Y and Deterioration Indicator)

Here, the correlation between the deterioration of the frying oil Y and each indicator of deterioration will be described with reference to FIG. 2 to FIG. 8. In the following, an example of the frying oil Y which has just been changed and thus has not been deteriorated may be referred to as "fresh frying oil Y1", while the frying oil Y that is repeatedly used and thus is deteriorated may be referred to as "deteriorated frying oil Y2".

Figure 2A:
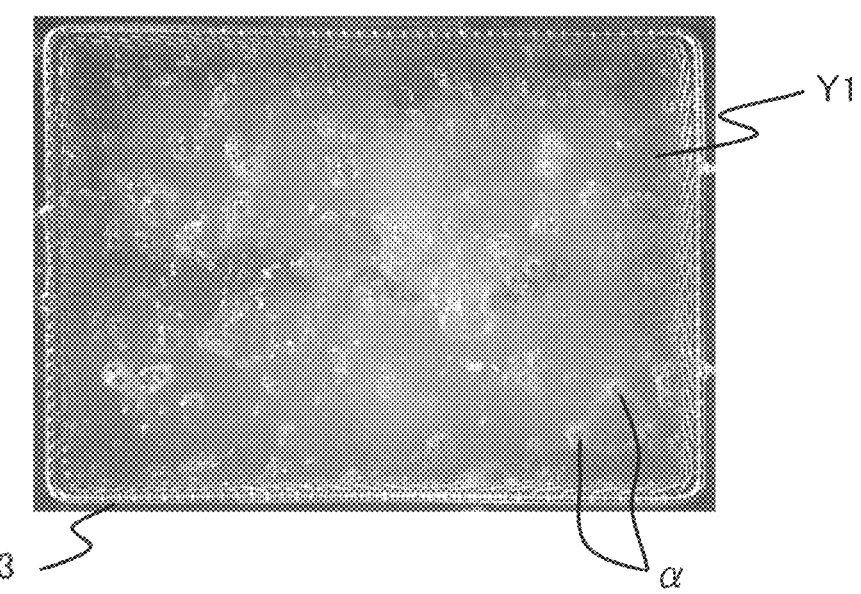
FIG. 2A illustrates a state in which a deep-fried food is being fried in fresh frying oil.
Figure 2B:
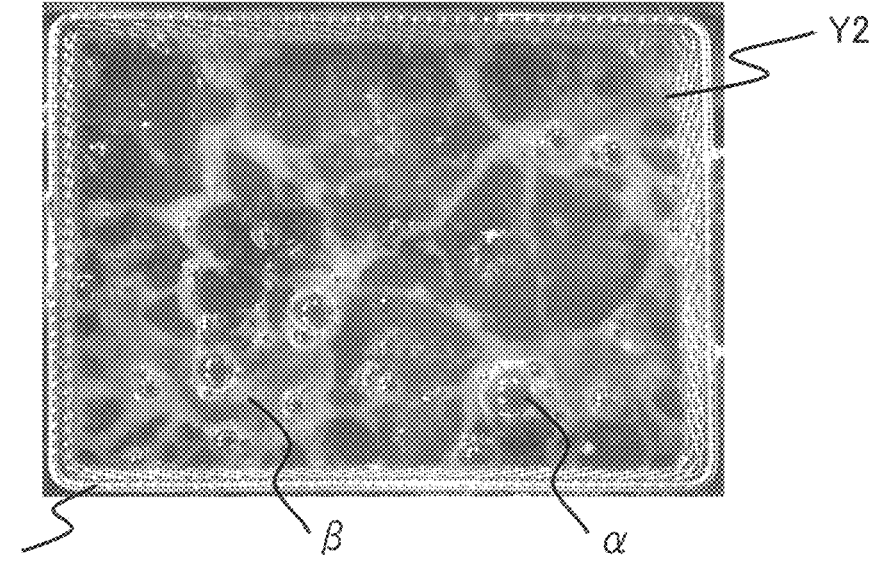
FIG. 2B illustrates a state in which a deep-fried food is being fried in deteriorated frying oil.

FIG. 2A and FIG. 2B illustrate examples of oil-surface images obtained when the fry basket 3 is imaged from above the fry basket 3 during deep-fry cooking. FIG. 2A illustrates a state in which the deep-fried food X is being fried in the fresh frying oil Y1, and FIG. 2B illustrates a state in which the deep-fried food X is being fried in the deteriorated frying oil Y2.

As illustrated in FIG. 2A and FIG. 2B, during deep-fry cooking, a plurality of air bubbles (surface air bubbles) rises to the surface of the frying oil Y. These air bubbles include, for example, an air bubble having a relatively large diameter (hereinafter, referred to as "large air bubble(s) α") and an air bubble having a relatively small diameter (hereinafter, referred to as "fine air bubble(s) β"). The large air bubbles α appear in both FIG. 2A and FIG. 2B. On the other hand, the number of fine air bubbles β appearing in FIG. 2B is more than that in FIG. 2A.

The large air bubbles α are likely to stay in that position to which they generate, while among the fine air bubbles, a few of them gather and form a stream on the oil surface B. In addition, as the frying oil Y deteriorates, the color of the frying oil Y darkens. This makes it more difficult to see the contour of the deep-fried food X in the deteriorated frying oil Y2 compared to the fresh frying oil Y1. Accordingly, using the level of visibility of the contour of the deep-fried food X as an indicator enables detection of the deterioration level of the frying oil Y2. In this case, the "difference" between the color of the deteriorated frying oil Y2 and the color of the region of the deep-fried food X is detected from the surface image of the deteriorated frying oil Y2. Note that it is also possible to estimate the deterioration level by detecting the "difference" between the color of the fresh frying oil Y1 and the color of the region of the deep-fried food X from the surface image of the fresh frying oil Y1 in advance and comparing both the "difference in color".

The major indicators (deterioration indicators) of deterioration of the frying oil Y are, for example, the viscosity of the frying oil Y, a rate of increase in viscosity, the acid value (AV) of the frying oil Y, the color tone of the frying oil Y, the anisidine value of the frying oil Y, the quantity of polar compounds of the frying oil Y, the carbonyl value of the frying oil Y, the smoke point of the frying oil Y, the tocopherol content of the frying oil Y, the iodine value of the frying oil Y, a refractive index of the frying oil Y, the quantity of volatile compounds of the frying oil Y, the composition of volatile compounds of the frying oil Y, the flavor of the frying oil Y, the quantity of volatile compounds of the deep-fried food X obtained by deep-fry cooking with the frying oil Y, the composition of volatile compounds of the deep-fried food X obtained by deep-fry cooking with the frying oil Y, and the flavor of the deep-fried food X obtained by deep-fry cooking with the frying oil Y. Selecting and using one or more deterioration indicators from among these deterioration indicators above enables detection of the deterioration of the frying oil Y.

For example, an increase rate of viscosity is a value calculated as a ratio of increase in the viscosity relative to the viscosity (viscosity at the start of use) measured before the deep-fried food X is fried for the first time in the fresh frying oil Y just after being changed. Note that the viscosity is a value which can be measured by an available viscometer, for example, an E-type viscometer (TVE-25H, made by Toki Sangyo Co., Ltd.)

Furthermore, for example, the acid value is a value measured by a method according to the standard methods for the analysis of fats, oils and related materials, 2.3.1-2013. The color tone is a value of (Y+10R) measured by a method according to the standard methods for the analysis of fats, oils and related materials, 2.2.1.1-2013. The anisidine value is a value measured by a method according to the standard methods for the analysis of fats, oils and related materials, 2.5.3-2013. The quantity of polar compounds is a value measured by a method according to the standard methods for the analysis of fats, oils and related materials, 2.5.5-2013 and an available instrument for measuring polar compounds (for example, made by Testo K.K.) based thereon.

Still further, the volatile compounds are compounds (odor components) that volatilize from the deep-fried food X and the frying oil Y, and the quantity and composition of the compounds change as the frying oil Y deteriorates. The volatile compounds are measured by a gas chromatograph-mass spectrometer (GC-MS), an odor sensor, or the like. In order to measure the flavor, a sensory evaluation (evaluation method involving the use of human senses by actually tasting) or a taste sensor are used. That is, the deterioration indicators of the frying oil Y include not only chemical deterioration indicators but also deterioration indicators in terms of taste.

As illustrated in FIG. 3 to FIG. 8, the degree of formation of air bubbles on the surface of the frying oil Y during deep-fry cooking correlates with the deterioration level of the frying oil Y. In particular, a strong correlation between the degree of formation of the "fine air bubbles β" and the deterioration level of the frying oil Y can be observed therefrom.

FIG. 3 to FIG. 5 illustrate examples of the correlations, each of which is between a ratio of the area (area ratio) of a region where air bubbles are formed (air bubble region) relative the total area in the oil surface image, which corresponds to the degree of formation of air bubbles, and a part of the deterioration indicators listed above. FIG. 6 to FIG. 8 illustrate examples of the correlations, each of which is between the number of air bubbles (regardless of the type of air bubbles) formed on the surface of the frying oil Y, which is identified from the oil surface image, and a part of the deterioration indicators. The correlation analysis illustrated in FIG. 3 to FIG. 8 is based on the analysis performed by, in the case of deep-frying four fried chickens to be deep-fried in the fryer 2 for 0-9 days, using the mean value of n=3 and dividing the mean value by 4 to convert it to a value per fried chicken.

Figure 3A:
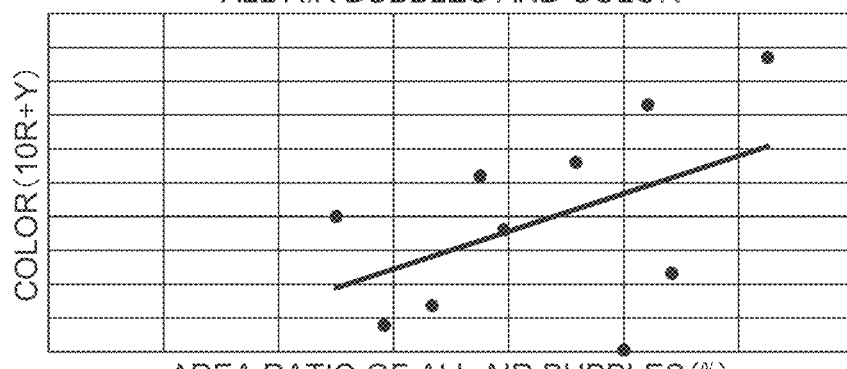
FIG. 3A is a graph illustrating a correlation between the area ratio of all air bubbles formed on a surface of frying oil and the color tone of the frying oil.
Figure 3B:
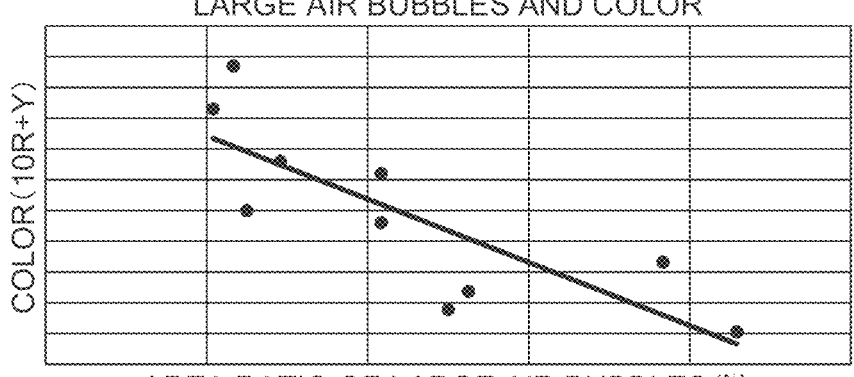
FIG. 3B is a graph illustrating a correlation between the area ratio of large air bubbles among air bubbles formed on a surface of frying oil and the color tone of the frying oil.
Figure 3C:
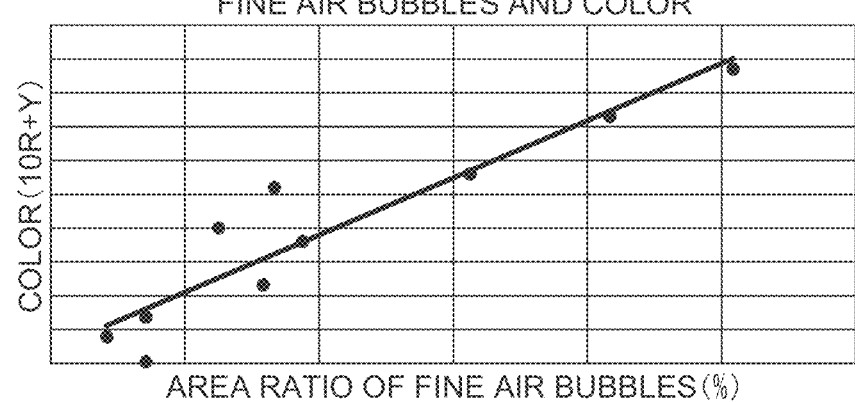
FIG. 3C is a graph illustrating a correlation between the area ratio of fine air bubbles among air bubbles formed on a surface of frying oil and the color tone of the frying oil.

FIG. 3A illustrates a correlation between the area ratio of all air bubbles formed on the surface of the frying oil Y and the color tone of the frying oil Y, FIG. 3B illustrates a correlation between the area ratio of the large air bubbles among the air bubbles formed on the surface of the frying oil Y and the color tone of the frying oil Y, and FIG. 3C illustrates a correlation between the area ratio of the fine air bubbles among the air bubbles formed on the surface of the frying oil Y and the color tone of the frying oil Y.

As illustrated in FIG. 3A and FIG. 3C, positive correlations are observed both between the area ratio of all the air bubbles and the color tone of the frying oil Y, and between the area ratio of the fine air bubbles and the color tone of the frying oil Y. In particular, a stronger positive correlation can be observed between the area ratio of the fine air bubbles β and the color tone of the frying oil Y. On the other hand, as illustrated in FIG. 3B, a negative correlation is observed between the area ratio of the large air bubbles α and the color tone of the frying oil Y.

It is known that the deterioration indicator "color tone" used in the exemplary graphs illustrated in FIG. 3A to FIG. 3C is positively correlated with the deterioration of the frying oil Y. Thus, in particular, estimating the color tone of the frying oil Y based on the area ratio of the fine air bubbles β enables precise determination of the deterioration of the frying oil Y.

Figure 4A:
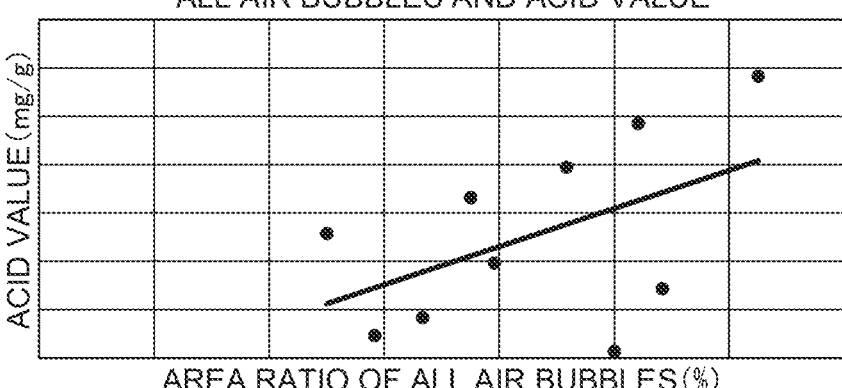
FIG. 4A is a graph illustrating a correlation between the area ratio of all air bubbles formed on a surface of frying oil and the acid value of the frying oil.
Figure 4B:
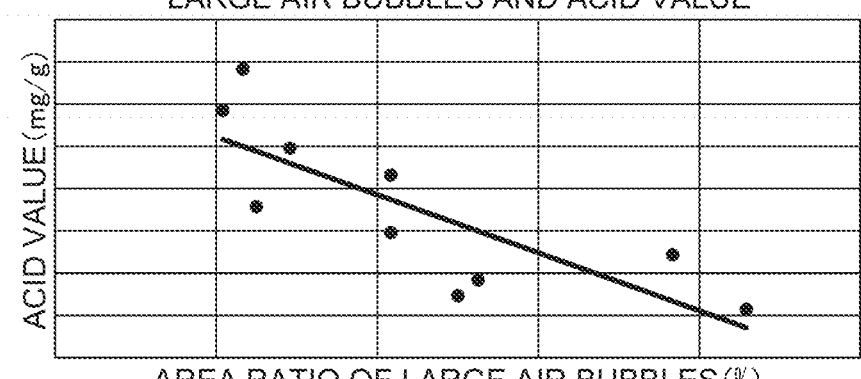
FIG. 4B is a graph illustrating a correlation between the area ratio of large air bubbles among air bubbles formed on a surface of frying oil and the acid value of the frying oil.
Figure 4C:
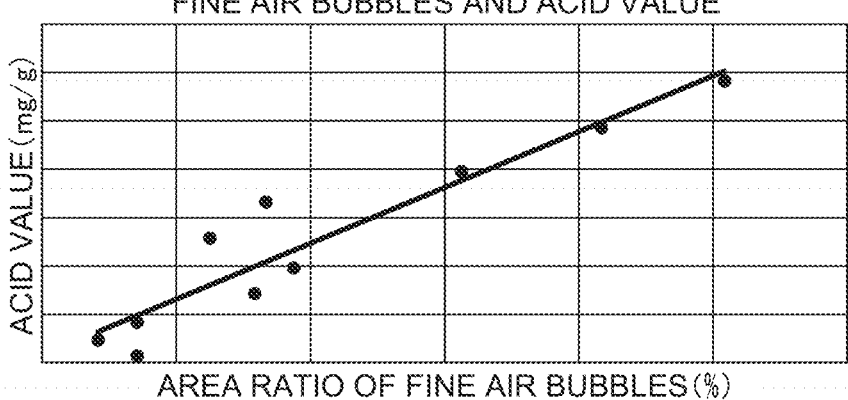
FIG. 4C is a graph illustrating a correlation between the area ratio of fine air bubbles among air bubbles formed on a surface of frying oil and the acid value of the frying oil.

FIG. 4A illustrates a correlation between the area ratio of all air bubbles formed on the surface of the frying oil Y and the acid value of the frying oil Y, FIG. 4B illustrates a correlation between the area ratio of the large air bubbles α among the air bubbles formed on the surface of the frying oil Y and the acid value of the frying oil Y, and FIG. 4C illustrates a correlation between the area ratio of the fine air bubbles β among the air bubbles formed on the surface of the frying oil Y and the acid value of the frying oil Y.

As illustrated in FIG. 4A and FIG. 4C, positive correlations are observed both between the area ratio of all the air bubbles and the acid value of the frying oil Y, and between the area ratio of the fine air bubbles β and the acid value of the frying oil Y. In particular, a stronger positive correlation can be observed between the area ratio of the fine air bubbles β and the acid value of the frying oil Y. On the other hand, as illustrated in FIG. 4B, a negative correlation is observed between the area ratio of the large air bubbles α and the acid value.

It is known that the deterioration indicator "acid value" used in the exemplary graphs illustrated in FIG. 4A to FIG. 4C is positively correlated with the deterioration of the frying oil Y. Thus, in particular, estimating the acid value of the frying oil Y based on the area ratio of the fine air bubbles β enables precise determination of the deterioration of the frying oil Y.

Figure 5A:
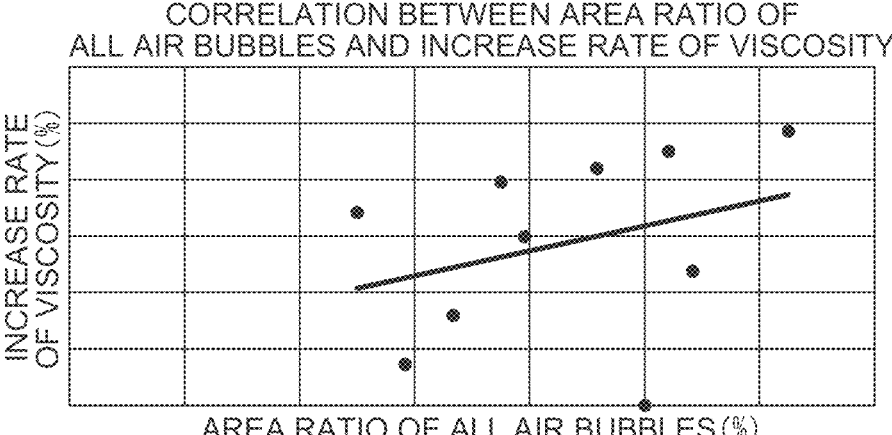
FIG. 5A is a graph illustrating a correlation between the area ratio of all air bubbles formed on a surface of frying oil and an increase rate of viscosity.
Figure 5B:
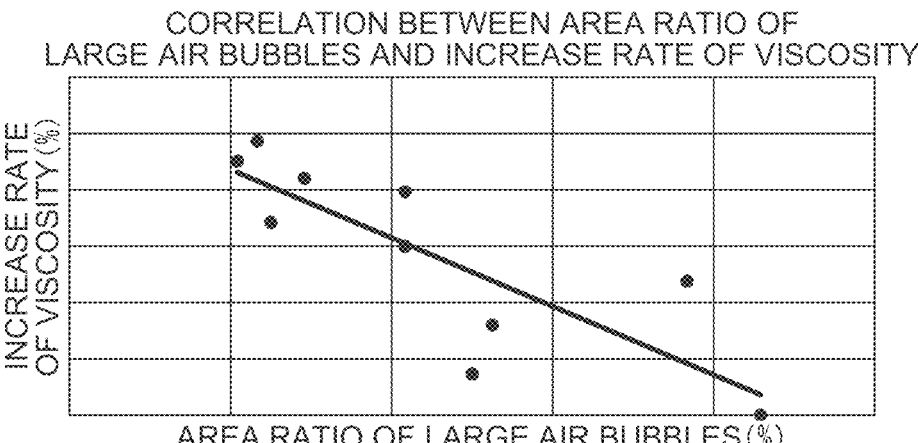
FIG. 5B is a graph illustrating a correlation between the area ratio of large air bubbles among air bubbles formed on a surface of frying oil and an increase rate of viscosity.
Figure 5C:
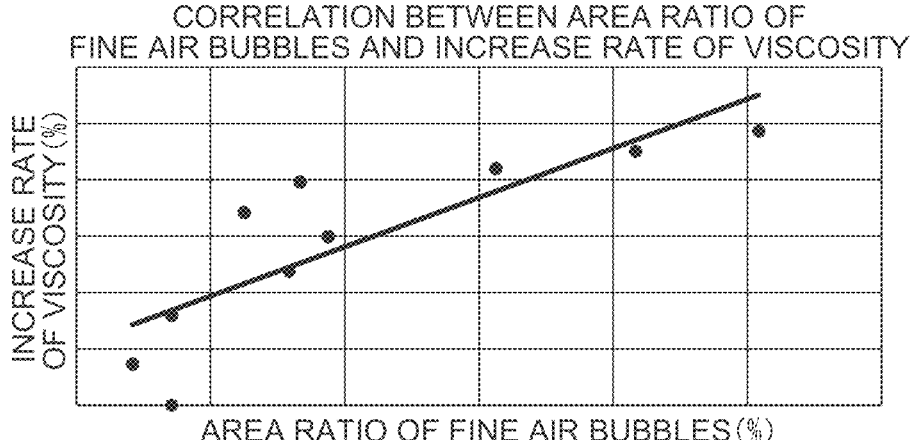
FIG. 5C is a graph illustrating a correlation between the area ratio of fine air bubbles among air bubbles formed on a surface of frying oil and an increase rate of viscosity.

FIG. 5A illustrates a correlation between the area ratio of all air bubbles formed on the surface of the frying oil Y and the increase rate of viscosity of the frying oil Y, FIG. 5B illustrates a correlation between the area ratio of the large air bubbles among the air bubbles formed on the surface of the frying oil Y and the increase rate of viscosity of the frying oil Y, and FIG. 5C illustrates a correlation between the area ratio of the fine air bubbles among the air bubbles formed on the surface of the frying oil Y and the increase rate of viscosity of the frying oil Y.

As illustrated in FIG. 5A and FIG. 5C, positive correlations are observed both between the area ratio of all the air bubbles and the increase rate of viscosity of the frying oil Y, and between the area ratio of the fine air bubbles β and the increase rate of viscosity of the frying oil Y. In particular, a stronger positive correlation can be observed between the area ratio of the fine air bubbles β and the increase rate of viscosity of the frying oil Y. On the other hand, as illustrated in FIG. 5B, a negative correlation is observed between the area ratio of the large air bubbles x and the increase ratio of viscosity of the frying oil Y.

It is known that the deterioration indicator "increase rate of viscosity" used in the exemplary graphs illustrated in FIG. 5A to FIG. 5C is positively correlated with the deterioration of the frying oil Y. Thus, in particular, estimating the increase rate of viscosity of the frying oil Y based on the area ratio of the fine air bubbles β enables precise determination of the deterioration of the frying oil Y.

FIG. 6A illustrates a correlation between the number of all air bubbles formed on the surface of the frying oil Y and the color tone of the frying oil Y, FIG. 6B illustrates a correlation between the number of large air bubbles α among the air bubbles formed on the surface of the frying oil Y and the color tone of the frying oil Y, and FIG. 6C illustrates a correlation between the number of fine air bubbles β among the air bubbles formed on the surface of the frying oil Y and the color tone of the frying oil Y.

As illustrated in FIG. 6A and FIG. 6C, positive correlations are observed both between the number of all the air bubbles and the color tone of the frying oil Y, and between the number of fine air bubbles β and the color tone of the frying oil Y. In particular, a stronger positive correlation can be observed between the number of fine air bubbles β and the color tone of the frying oil Y. On the other hand, as illustrated in FIG. 6B, a negative correlation is observed between the number of large air bubbles α and the color tone of the frying oil Y.

It is known that the deterioration indicator "color tone" used in the exemplary graphs illustrated in FIG. 6A to FIG. 6C is positively correlated with the deterioration of the frying oil Y. Thus, in particular, estimating the color tone of the frying oil Y based on the number of fine air bubbles β enables precise determination of the deterioration of the frying oil Y.

Figure 7A:
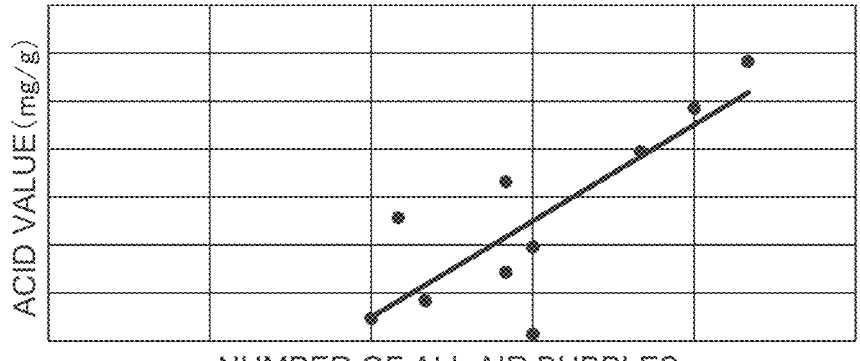
FIG. 7A is a graph illustrating a correlation between the number of all air bubbles formed on a surface of frying oil and the acid value.
Figure 7B:
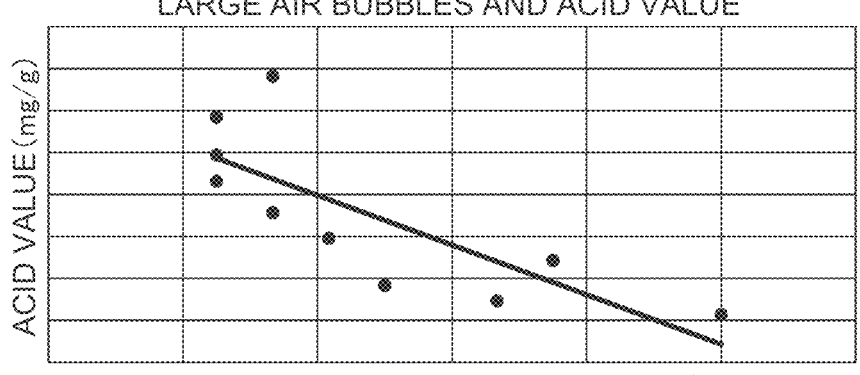
FIG. 7B is a graph illustrating a correlation between the number of large air bubbles among air bubbles formed on a surface of frying oil and the acid value.
Figure 7C:
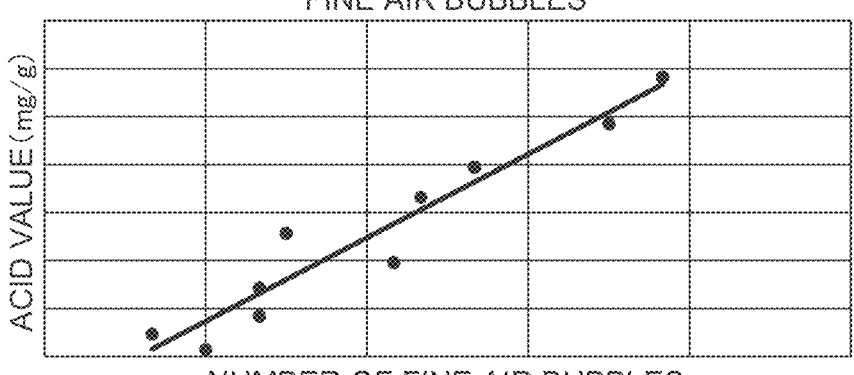
FIG. 7C is a graph illustrating a correlation between the number of fine air bubbles among air bubbles formed on a surface of frying oil and the acid value.

FIG. 7A illustrates a correlation between the number of all air bubbles formed on the surface of the frying oil Y and the acid value of the frying oil Y, FIG. 7B illustrates a correlation between the number of large air bubbles among the air bubbles formed on the surface of the frying oil Y and the acid value of the frying oil Y, and FIG. 7C illustrates a correlation between the number of fine air bubbles among the air bubbles formed on the surface of the frying oil Y and the acid value of the frying oil Y.

As illustrated in FIG. 7A and FIG. 7C, positive correlations are observed both between the number of all the air bubbles and the acid value of the frying oil Y, and between the number of fine air bubbles β and the acid value of the frying oil Y. In particular, a stronger positive correlation can be observed between the number of fine air bubbles β and the acid value of the frying oil Y. On the other hand, as illustrated in FIG. 7B, a negative correlation is observed between the number of large air bubbles α and the acid value of the frying oil Y.

It is known that the deterioration indicator "acid value" used in the exemplary graphs illustrated in FIG. 7A to FIG. 7C is positively correlated with the deterioration of the frying oil Y. Thus, in particular, estimating the acid value of the frying oil Y based on the number of fine air bubbles β enables precise determination of the deterioration of the frying oil Y.

Figure 8A:
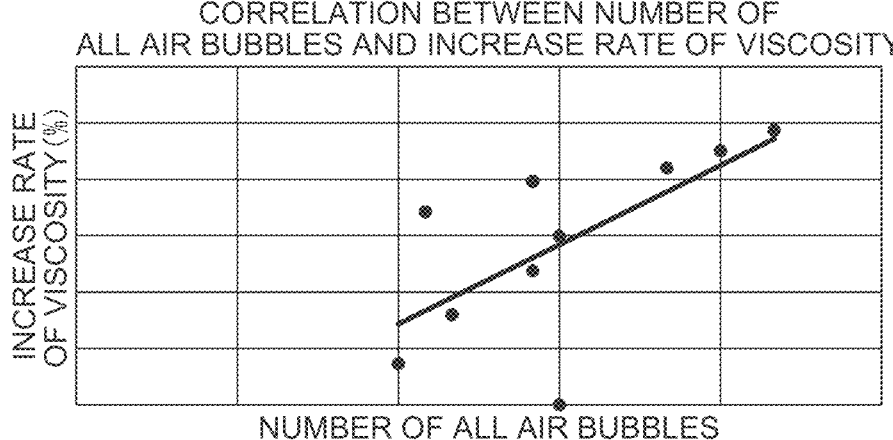
FIG. 8A is a graph illustrating a correlation between the number of all air bubbles formed on a surface of frying oil and an increase rate of viscosity.
Figure 8B:
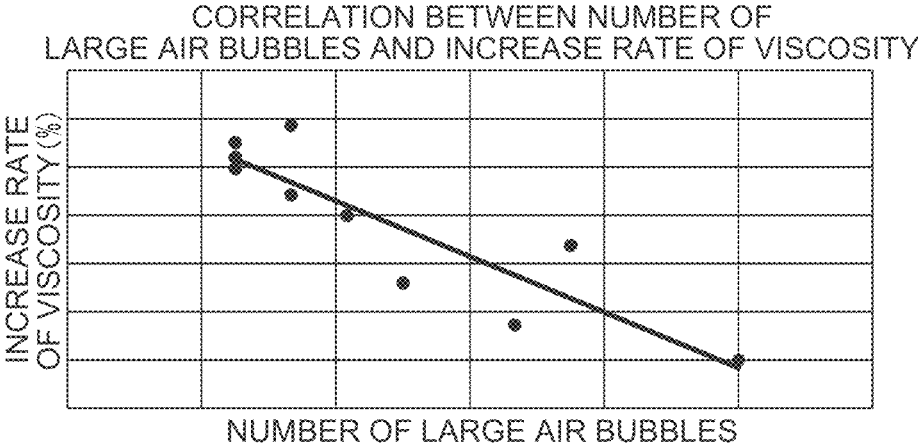
FIG. 8B is a graph illustrating a correlation between the number of large air bubbles formed on a surface of frying oil and an increase rate of viscosity.
Figure 8C:
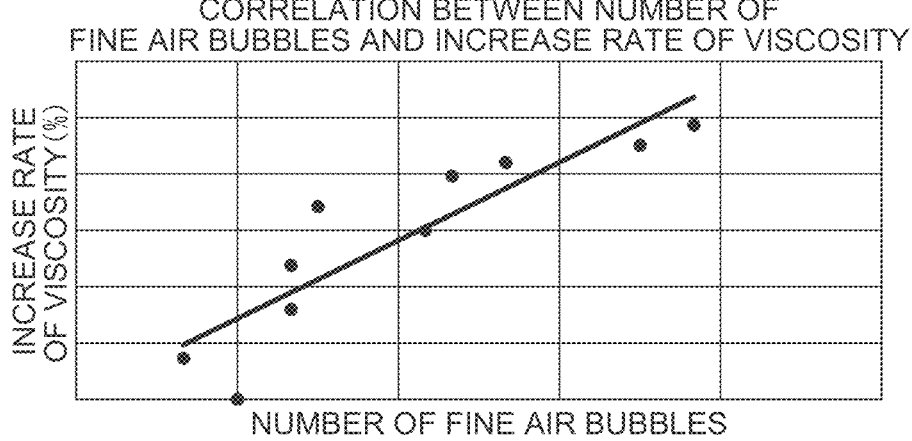
FIG. 8C is a graph illustrating a correlation between the number of fine air bubbles formed on a surface of frying oil and an increase rate of viscosity.

FIG. 8A illustrates a correlation between the number of all air bubbles formed on the surface of the frying oil Y and the increase rate of viscosity of the frying oil Y, FIG. 8B illustrates a correlation between the number of large air bubbles α among the air bubbles formed on the surface of the frying oil Y and the increase rate of viscosity of the frying oil Y, and FIG. 8C illustrates a correlation between the number of fine air bubbles β among the air bubbles formed on the surface of the frying oil Y and the increase rate of viscosity of the frying oil Y.

As illustrated in FIG. 8A and FIG. 8C, positive correlations are observed both between the number of all the air bubbles and the increase rate of viscosity of the frying oil Y, and between the number of fine air bubbles β and the increase rate of viscosity of the frying oil Y. In particular, a stronger positive correlation can be observed between the number of fine air bubbles β and the increase rate of viscosity of the frying oil Y. On the other hand, as illustrated in FIG. 8B, a negative correlation is observed between the number of large air bubbles x and the increase rate of viscosity of the frying oil Y.

It is known that the deterioration indicator "increase rate of viscosity" used in the exemplary graphs illustrated in FIG. 8A to FIG. 8C is positively correlated with the deterioration of the frying oil Y. Thus, in particular, estimating the increase rate of viscosity of the frying oil Y based on the number of fine air bubbles β enables precise determination of the deterioration of the frying oil Y.

As described above, it can be observed that the fine air bubbles β among all air bubbles formed on the surface of the frying oil Y are correlated with the deterioration indicators more strongly than all the air bubbles and the large air bubbles α (see FIG. 3C, FIG. 4C, FIG. 5C, FIG. 6C, FIG. 7C, and FIG. 8C). Therefore, in order to determine the deterioration of the frying oil Y precisely, it is desirable to focus on the fine air bubbles β more than all the air bubbles or the large air bubbles α.

As described above, the area ratio of the fine air bubbles β and the number of fine air bubbles β are feature parameters characterizing the deterioration of the frying oil Y. In addition to the area ratio of the fine air bubbles β and the number of fine air bubbles β, the feature parameters include one or more indicators selected from the speed of disappearance of air bubbles, the presence or absence of a stream of the fine air bubbles β, the difference between the color of the frying oil Y and the color of the region of the deep-fried food X (visibility level of the contour of the deep-fried food X), and a cumulative value of the area of air bubbles. Hereinafter, a deterioration level determination device 5 for determining the deterioration level of the frying oil Y will be described for each embodiment.

First Embodiment

The deterioration level determination device 5 according to a first embodiment of the present invention will be described with reference to FIG. 9 to FIG. 16.
(Configuration of deterioration level determination device 5)
A configuration of the deterioration level determination device 5 will be described with reference to FIG. 9 to FIG. 15.

FIG. 9 is a functional block diagram illustrating functions of the deterioration level determination device 5.

The deterioration level determination device 5 has a function to receive, as input data, an oil surface image which is an image of the surface of the frying oil Y directly from the video camera 42 or indirectly via an external storage medium, further or from a remote location via a communication line, and output, as output data, a result of determination of the deterioration level of the frying oil Y. Furthermore, the deterioration level determination device 5 has a function to notify the outside, such as a user, of the determination result.

As in the case of general computers, the deterioration level determination device 5 includes, as hardware resources, a hardware configuration in which a CPU, a RAM, a ROM, an HDD, an input I/F, and an output I/F are connected to each other via a bus. The oil surface image is input via the input I/F as the image data acquired by the imaging device such as the video camera 42. The oil surface image which has been input is displayed via an image display means such as the monitor 41 connected to the output I/F.

In this hardware configuration, the CPU reads a control program (software) stored in a recording medium such as the ROM, the HDD, or an optical disc and loads it on the RAM so as to execute the loaded control program, whereby each function of the deterioration level determination device 5 can be implemented by the cooperation of the control program and the hardware resources.

Note that, in the present embodiment, the deterioration level determination device 5 is described as a computer composed of a combination of software and hardware, however, the present invention is not limited thereto. As one of the examples of configurations of other computers, an integrated circuit for implementing functions of a control program executed at the fryer 2 side may be used.

The deterioration level determination device 5 includes an oil surface image acquisition section 50, an air bubble image extraction section 51, an air bubble dimension calculation section 52, a feature region identification section 53, a feature parameter calculation section 54, a deterioration indicator estimation section 55, a deterioration level determination section 56, a replacement timing decision section 57, a selection section 58, a notification section 59, and a storage section 500.

The oil surface image acquisition section 50 is configured to acquire image data (oil surface image data) of an image of the surface of the frying oil Y (oil surface image) based on an image of the fry basket 3 captured by the video camera 42. For example, in the case that the image of the fry basket 3 to be input is a still image, the oil surface image acquisition section 50 extracts the contour of the fry basket 3 and acquires only the inside of the contour so as to obtain the oil surface image to be processed. In the case that the image of the fry basket 3 is a moving image, the oil surface image acquisition section 50 decomposes the moving image into frames composing the moving image (for example, if it is a moving image of 30 fps, decomposes it into images every ⅟30 second), and extract the contour of the fry basket 3 included in each frame so as to acquire only the inside of the contour as the oil surface image.

The air bubble image extraction section 51 is configured to extract, as an "air bubble image", a portion (region) of the air bubbles formed due to deep-fry cooking from the oil surface image acquired by the oil surface image acquisition section 50. For example, the air bubble image extraction section 51 executes the contour extraction image processing using the filter processing with respect to the oil surface image so as to extract an image of a region including a portion that matches the feature of an air bubble (for example, approximates a circular shape) from a portion forming the contour (portion indicating a certain enclosed region) included in the oil surface image.

The air bubble dimension calculation section 52 is configured to calculate a size R of a region that can be determined as an air bubble included in the air bubble image extracted by the air bubble image extraction section 51. Here, the "size R" means a "scale indicating the size of an air bubble" which shall be obtained when the air bubble is actually measured, such as the diameter, outer diameter, or circumference of each air bubble included in the oil surface image. That is, the air bubble dimension calculation section 52 calculates, as a numerical value, the size R of each "air bubble" included in the air bubble image which has been cut out by the image processing executed with respect to the oil surface image.

The feature region identification section 53 is configured to identify, as a "feature region", a region including an air bubble whose size R falls within a specific range in comparison with a specific threshold value, from among the air bubbles obtained by the calculation in the air bubble dimension calculation section 52. Specifically, the feature region identification section 53 determines whether the size R of each air bubble obtained by the calculation in the bubble dimension calculation section 52 is less than a dimension threshold value Rth. Then, the feature region identification section 53 identifies, as the feature region, a partial region including an air bubble whose size R is determined as being less than the dimension threshold value Rth (for example, 2.5 mm) (R<Rth) as a result of the determination. That is, the feature region corresponds to further a portion of the partial region corresponding to a portion of the entire region of the oil surface image.

In the present embodiment, the feature parameter calculation section 54 is configured to calculate a feature parameter F in the feature region identified by the feature region identification section 53. The "feature parameter(s) F"

includes information based on a plurality of numerical values. For example, the "feature parameter F" may include the "area ratio", which is a ratio of the area of the feature region including the "fine air bubble β" which is an air bubble whose size R corresponds to the dimension threshold value Rth relative to the total area of the oil surface. The number of "fine air bubbles" included in the feature region also corresponds to the "feature parameter F".

Furthermore, the disappearance speed (elapsed time from formation to disappearance) of each air bubble, the presence or absence of fluctuation (stream) of the positions of the "fine air bubbles β" in the oil surface within the feature region and its adjacent region, the difference between the color of the frying oil Y and the color of the region of the deep-fried food X, and a cumulative value of the area of the air bubbles also correspond to the "feature parameter F", respectively. The feature parameter calculation section 54 calculates all or a part of the plurality of "feature parameters F" listed above.

The "disappearance speed of each air bubble" corresponds to an elapsed time from formation of each air bubble on the surface of the frying oil Y during deep-fry cooking to disappearance thereof. That is, a relatively short elapsed time from formation to disappearance corresponds to the "high disappearance speed" while a relatively long elapsed time corresponds to the "low disappearance speed".

In the case of using the disappearance speed of each air bubble as the feature parameter F, since it is not limited to the disappearance speed of the fine air bubble β, the feature parameter calculation section 54 may calculate the disappearance speed of the large air bubbles α included in the air bubble image extracted by the air bubble image extraction section 51. That is, the deterioration level determination device 5 does not necessarily have to include the air bubble dimension calculation section 52 and the feature region identification section 53.

Here, the "cumulative value of the area of air bubbles" will be described with reference to FIG. 19. FIG. 19 is a diagram for explaining a method of calculating a cumulative value of the area of air bubbles in the deterioration level determination device 5. As illustrated in the upper part of FIG. 19, firstly, the feature parameter calculation section 54 calculates, as the "value of the area of air bubbles", the ratio of the area (area ratio) of air bubbles (including the large air bubbles α and the fine air bubbles β) relative to the total area of the oil surface based on the oil surface image acquired by the oil surface image acquisition section 50 and the air bubble image extracted by the air bubble image extraction section 51. Subsequently, as illustrated in the lower part of FIG. 19, the feature parameter calculation section 54 accumulates the value of the area of the air bubbles calculated over time within a predetermined period of time (for example, 30 minutes) so as to obtain the "cumulative value of the area of air bubbles".

In the same manner as the disappearance speed of each air bubble described above, in the case of using the cumulative value of the area of air bubbles as the feature parameter F, the feature parameter calculation section 54 may calculate the cumulative value of the area of all air bubbles included in the air bubble image extracted by the air bubble image extraction section 51, may calculate the cumulative value of the area of the large air bubbles α included in the air bubble image extracted by the air bubble image extraction section 51, or may calculate the cumulative value of the area of the fine air bubbles β included in the air bubble image extracted by the air bubble image extraction section 51.

The deterioration indicator estimation section 55 is configured to estimate a deterioration indicator DI of the frying oil Y based on the feature parameter F calculated by the feature parameter calculation section 54. Specifically, the deterioration indicator estimation section 55 estimates the deterioration indicator DI corresponding to the feature parameter F in accordance with a correlation between each feature parameter F illustrated in FIG. 10 to FIG. 14 and the deterioration indicator DI. In this connection, the "color tone of the frying oil Y" which is the deterioration indicator DI does not necessarily matches the "color tone of the frying oil Y obtainable based on the oil surface image", however, the correspondence between the "color tone of the frying oil Y" and the "color tone of the frying oil Y obtainable based on the oil surface image" is stored in the storage section 500 of the deterioration level determination device 5, and thus the "color tone of the frying oil Y obtainable based on the oil surface image" is converted to the "color tone of the frying oil Y" based on the correspondence.

Figure 10A:
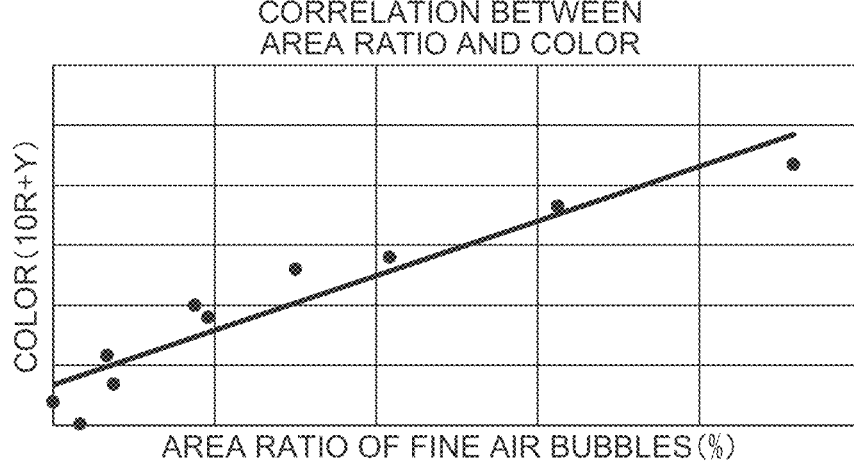
FIG. 10A is a graph illustrating a correlation between the area ratio of fine air bubbles and the color tone.
Figure 10B:
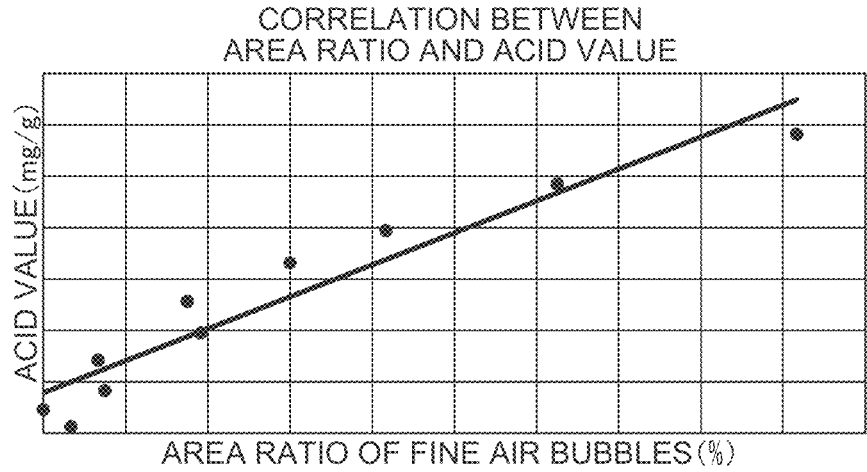
FIG. 10B is a graph illustrating a correlation between the area ratio of fine air bubbles and the acid value.
Figure 10C:
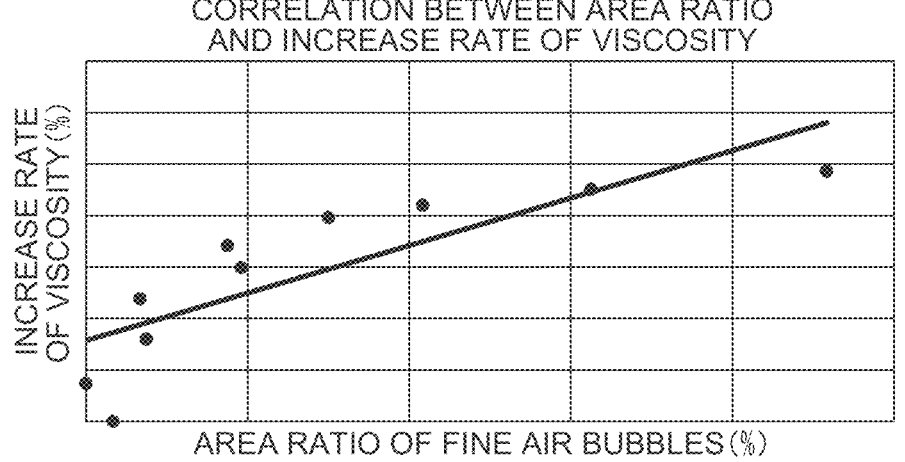
FIG. 10C is a graph illustrating a correlation between the area ratio of fine air bubbles and the increase rate of viscosity.

FIG. 10A illustrates a correlation between the area ratio of the fine air bubbles β and the color tone of the frying oil Y, FIG. 10B illustrates a correlation between the area ratio of the fine air bubbles β and the acid value of the frying oil Y, and FIG. 10C illustrates a correlation between the area ratio of the fine air bubbles β and the increase rate of viscosity of the frying oil Y. Positive correlations are observed between the area ratio of the fine air bubbles β and the color tone of the frying oil Y, the acid value of the frying oil Y, and the increase rate of viscosity of the frying oil Y, respectively.

Figure 11A:
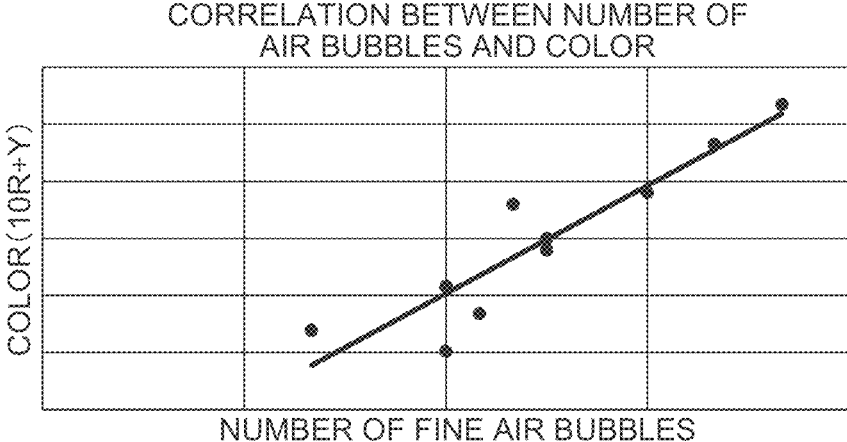
FIG. 11A is a graph illustrating a correlation between the number of fine air bubbles and the color tone.
Figure 11B:
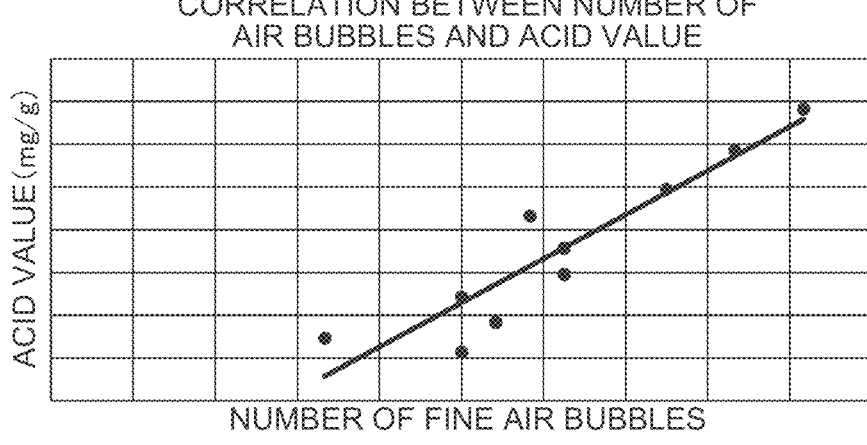
FIG. 11B is a graph illustrating a correlation between the number of fine air bubbles and the acid value.
Figure 11C:
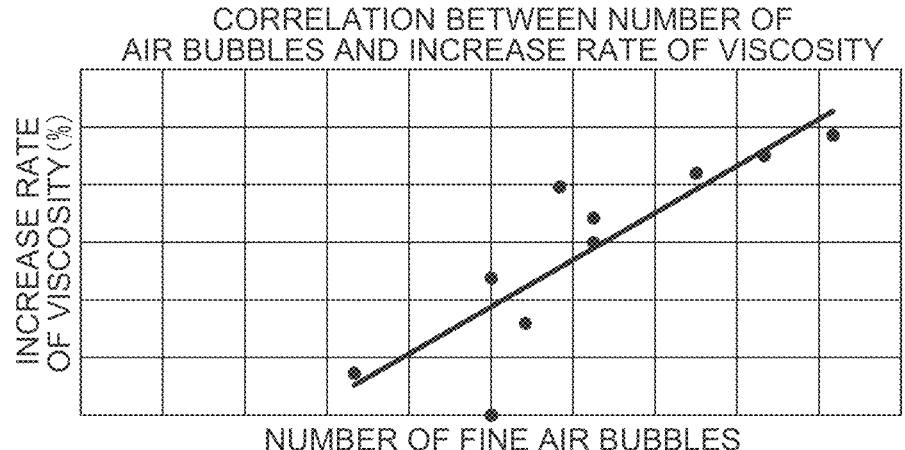
FIG. 11C is a graph illustrating a correlation between the number of fine air bubbles and the increase rate of viscosity.

FIG. 11A illustrates a correlation between the number of fine air bubbles β and the color tone of the frying oil Y, FIG. 11B illustrates a correlation between the number of fine air bubbles β and the acid value of the frying oil Y, and FIG. 11C illustrates a correlation between the number of fine air bubbles β and the increase rate of viscosity of the frying oil Y. Positive correlations are observed between the number of fine air bubbles β and the color tone of the frying oil Y, the acid value of the frying oil Y, and the increase rate of viscosity of the frying oil Y, respectively.

Figure 12A:
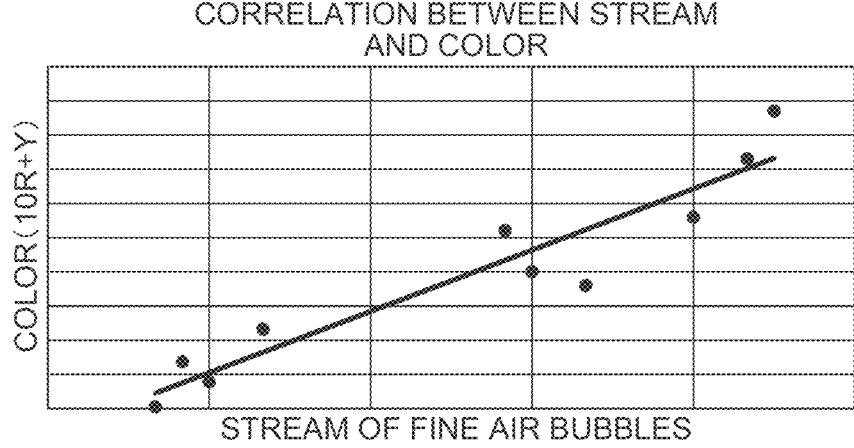
FIG. 12A is a graph illustrating a correlation between the stream of fine air bubbles and the color tone.
Figure 12B:
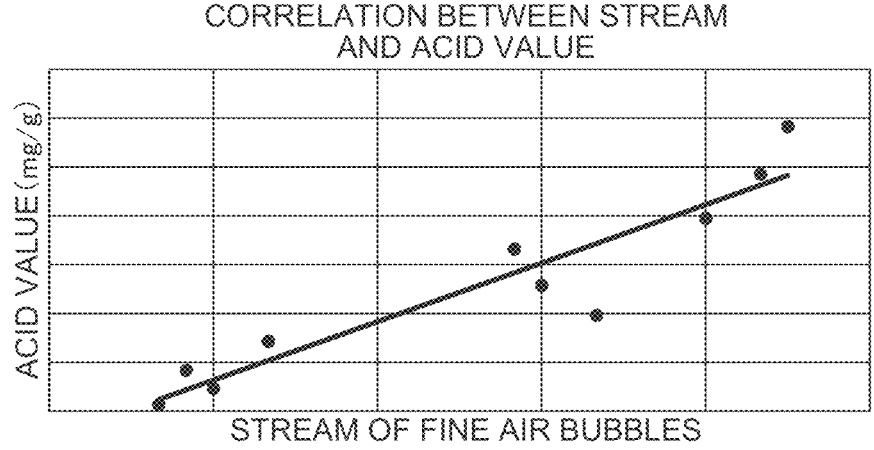
FIG. 12B is a graph illustrating a correlation between the stream of fine air bubbles and the acid value.
Figure 12C:
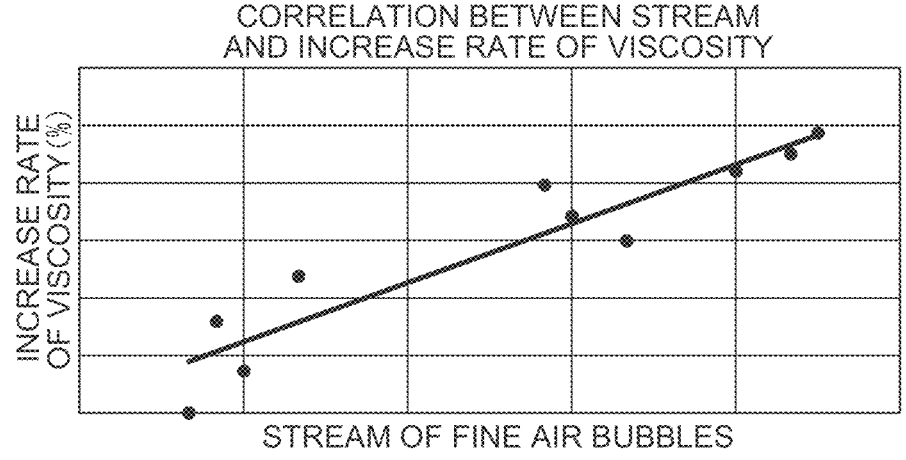
FIG. 12C is a graph illustrating a correlation between the stream of fine air bubbles and the increase rate of viscosity.

FIG. 12A illustrates a correlation between the stream of the fine air bubbles β and the color tone of the frying oil Y, FIG. 12B illustrates a correlation between the stream of the fine air bubbles β and the acid value of the frying oil Y, and FIG. 12C illustrates a correlation between the stream of the fine air bubbles β and the increase rate of viscosity of the frying oil Y. Positive correlations are observed between the stream of the fine air bubbles β and the color tone of the frying oil Y, the acid value of the frying oil Y, and the increase rate of viscosity of the frying oil Y, respectively.

Figure 13A:
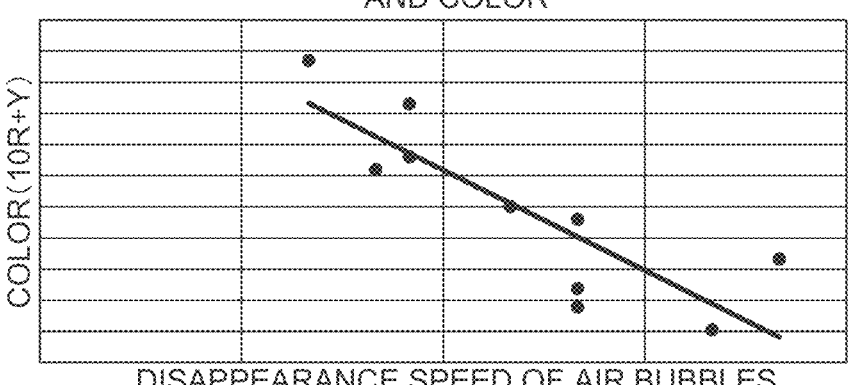
FIG. 13A is a graph illustrating a correlation between the disappearance speed of air bubbles and the color tone.
Figure 13B:
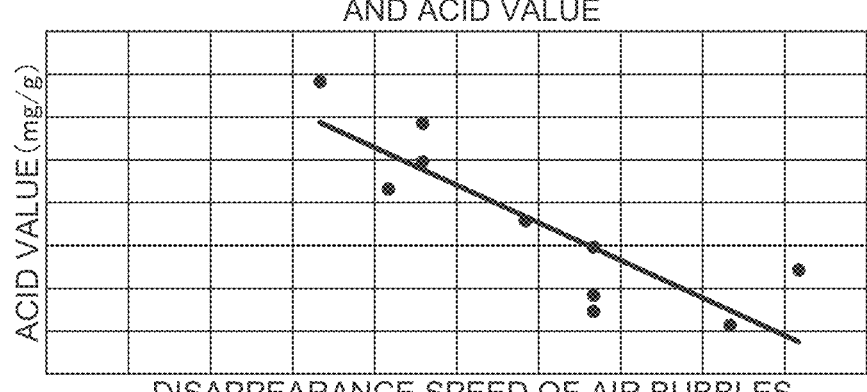
FIG. 13B is a graph illustrating a correlation between the disappearance speed of air bubbles and the acid value.
Figure 13C:
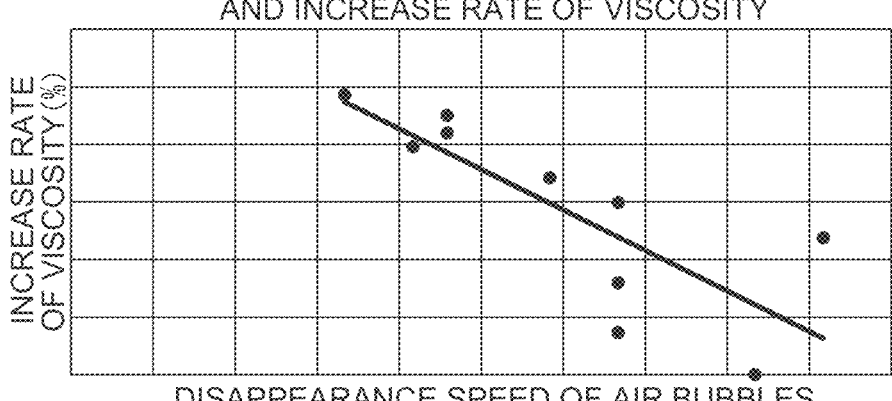
FIG. 13C is a graph illustrating a correlation between the disappearance speed of air bubbles and the increase rate of viscosity.

FIG. 13A illustrates a correlation between the disappearance speed of the air bubbles and the color tone of the frying oil Y, FIG. 13B illustrates a correlation between the disappearance speed of the air bubbles and the acid value of the frying oil Y, and FIG. 13C illustrates a correlation between the disappearance speed of the air bubbles and the increase rate of viscosity of the frying oil Y. Negative correlations are observed between the disappearance speed of the air bubbles and the color tone of the frying oil Y, the acid value of the frying oil Y, and the increase rate of viscosity of the frying oil Y, respectively. This is because, as the frying oil Y deteriorates, the viscosity of the frying oil Y increases, which makes the air bubbles less likely to disappear.

FIG. 14A illustrates a correlation between the visibility level of the contour of the deep-fried food X and the color tone of the frying oil Y, FIG. 14B illustrates a correlation between the visibility level of the contour of the deep-fried food X and the acid value of the frying oil Y, and FIG. 14C illustrates a correlation between the visibility level of the contour of the deep-fried food X and the increase rate of viscosity of the frying oil Y. Negative correlations are observed between the visibility level of the contour of the deep-fried food X and the color tone of the frying oil Y, the acid value of the frying oil Y, and the increase rate of viscosity of the frying oil Y, respectively.

Figure 20A:
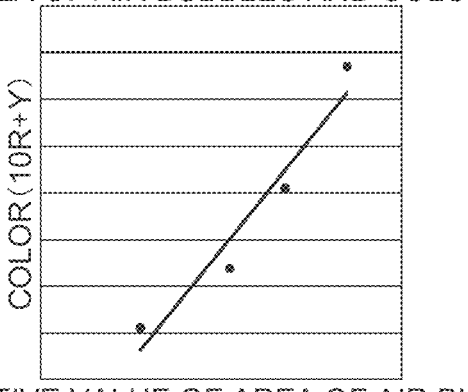
FIG. 20A is a graph illustrating a correlation between the cumulative value of the area of air bubbles and the color tone.
Figure 20B:
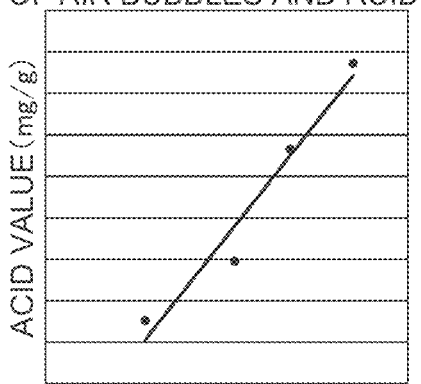
FIG. 20B is a graph illustrating a correlation between the cumulative value of the area of air bubbles and the acid value.
Figure 20C:
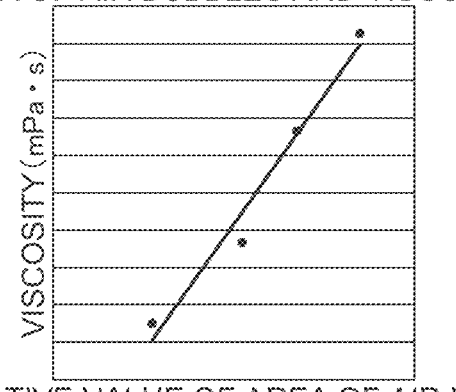
FIG. 20C is a graph illustrating a correlation between the cumulative value of the area of air bubbles and the viscosity.

FIG. 20A illustrates a correlation between the cumulative value of the area of air bubbles and the color tone of the frying oil Y, FIG. 20B illustrates a correlation between the cumulative value of the area of air bubbles and the acid value of the frying oil Y, and FIG. 20C illustrates a correlation between the cumulative value of the area of air bubbles and the viscosity of the frying oil Y. Positive correlations are observed between the cumulative value of the area of air bubbles and the color tone of the frying oil Y, the acid value of the frying oil Y, and the viscosity of the frying oil Y, respectively.

Figure 15:
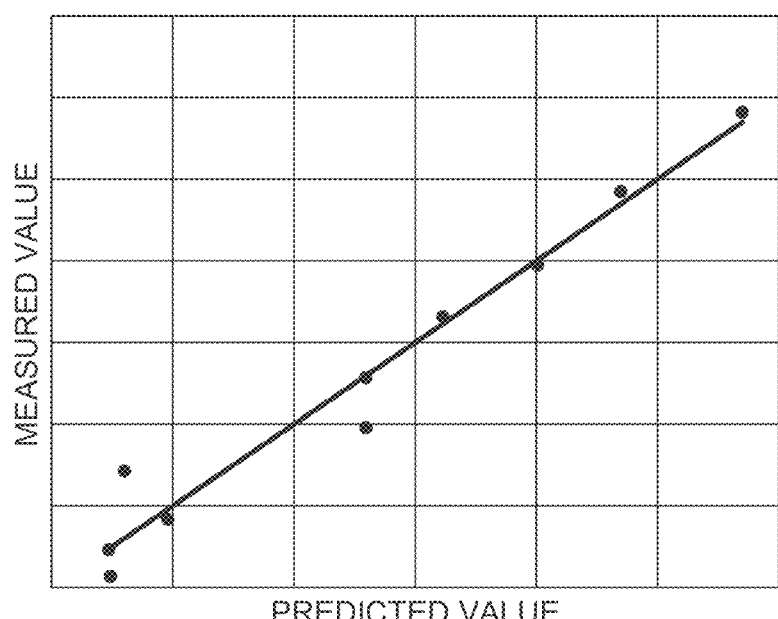
FIG. 15 is a graph illustrating a correlation between a predicted value and measured value of the acid value.

Note that it is preferable to use a combination of the feature parameters F such as the area ratio of the fine air bubbles β, the number of fine air bubbles β, the disappearance speed of air bubbles, the stream of the fine air bubbles β, the visibility level of the contour of the deep-fried food X, and the cumulative value of the area of the air bubbles. Combining the feature parameters F can improve the precision of estimation of the deterioration indicator DI. For example, when OPLS analysis (orthogonal projection partial least squares regression) for predicting the acid value of the frying oil Y is performed using a combination of the five feature parameters F, which are the area ratio of the fine air bubbles β, the number of fine air bubbles β, the disappearance speed of air bubbles, the stream of the fine air bubbles β, and the visibility level of the contour of the deep-fried food X, as illustrated in FIG. 15, a positive correlation is found between a predicted value and a measured value. This shows that combining the multiple feature parameters F enables improvement in the precision of prediction of the acid value of the frying oil Y by the indicator relating to the "air bubbles" which can be identified from on the oil surface image when compared to the case of using each of the feature parameters F separately for the prediction.

The deterioration level determination section 56 is configured to determine the deterioration level of the frying oil Y based on the deterioration indicator DI estimated by the deterioration indicator estimation section 55. When the deterioration indicator DI corresponds to a deterioration threshold value DIth (DI=DIth), the deterioration level is 100%, and thus the frying oil Y needs to be changed. When the deterioration indicator DI is less than the deterioration threshold value DIth (DI<DIth), the deterioration level is, for example, 50%, 75%, or the like.

The deterioration threshold value DIth indicating the level of 100% deterioration can be arbitrarily set. For example, it is assumed that a user A sets the acid value 2.5 to the deterioration threshold value DIth (DIth=2.5) and a user B sets the acid value 2.0 to the deterioration threshold value DIth (DIth=2.0). In this case, when both the frying oil Y used for deep-fry cooking performed by the user A and the frying oil Y used for deep-fry cooking performed by the user B have the acid value of 1.0, the deterioration level determination section 56 determines that the deterioration level of the frying oil Y in use by the user A is 40% and the deterioration level of the frying oil Y in use by the user B is 50%.

The replacement timing decision section 57 is configured to decide whether it is necessary to change the frying oil Y based on the deterioration level determined by the deterioration level determination section 56.

The selection section 58 is configured to select, based on the deterioration level determined by the deterioration level determination section 56, the type of the deep-fried food X which can be deep-fried for the next using the frying oil Y and the number of pieces thereof for each type. Since, depending on the type of the deep-fried food X, the color of the frying oil Y may darken more and/or the viscosity thereof may increase more, and vice versa, the amount of variation of each of the deterioration indicators differs depending on the type of the deep-fried food X. For example, when the deterioration level determination section 56 determines that the deterioration level is 70%, the selection section 58 selects one deep-fried mashed potato or two spring rolls based on the correlation between the deterioration level and the type of the deep-fried food X and the number of pieces thereof for each type.

As described above, since, depending on the deterioration level of the frying oil Y, the deep-fried food X suitable for the next deep-fry cooking is selected based on the amount of variation of the deterioration indicator DI, the frying oil Y can be used such that each deterioration indicator DI can reach the deterioration threshold value DIth at the same time. In addition, for example, if the selection section 58 selects the deep-fried food X of the type which absorbs a large amount of oil and the selected deep-dried food X is fried, mixing fresh oil (adding fresh oil) thereinto by the amount of oil reduced from a predetermined amount of oil can cause a time for disposing the frying oil Y to be delayed. This can support the efficient use of the frying oil Y. Furthermore, decrease in the stock quantity of the deep-fried food X in the stores can be managed based on the information of the deep-fried food X selected by the selection section 58, whereby ordering and receiving of the deep-fried food X can be performed based thereon.

The notification section 59 is configured to output a display signal related to the deterioration level determined by the deterioration level determination section 56 to the monitor 41. The monitor 41 displays, for example, "present deterioration level of frying oil Y is 00%".

Furthermore, when the replacement timing decision section 57 decides that it is time for changing the frying oil Y, the notification section 59 outputs, to the monitor 41, a display signal for displaying the determination result on the monitor 41. The monitor 41 displays, for example, "please change frying oil".

Still further, when the selection section 58 selects the type of the deep-fried food X which can be deep-fried for the next using the frying oil Y and the number of pieces thereof for each type, the notification section 59 outputs, to the monitor 41, a display signal for displaying the selection result and items relating to the selection result on the monitor 41. The monitor 41 displays, for example, "there are ○ more pieces left that remain unfried", "you can deep-fry ○ pieces of ○○ or ● pieces of ●● for the next", "add fresh oil now, and you can use this oil for ○ days later", and the like.

The storage section 500 is configured to retain the dimension threshold value Rth, the correlation between each feature parameter F illustrated in FIG. 10 to FIG. 14 and the deterioration indicator DI, the deterioration threshold value DIth, and the correlation between the deterioration level and the type of the deep-fried food X and the number of pieces thereof for each type.

(Processing in Deterioration Level Determination Device 5)

Next, a flow of the specific processing executed in the deterioration level determination device 5 will be described with reference to FIG. 16.

Figure 16:
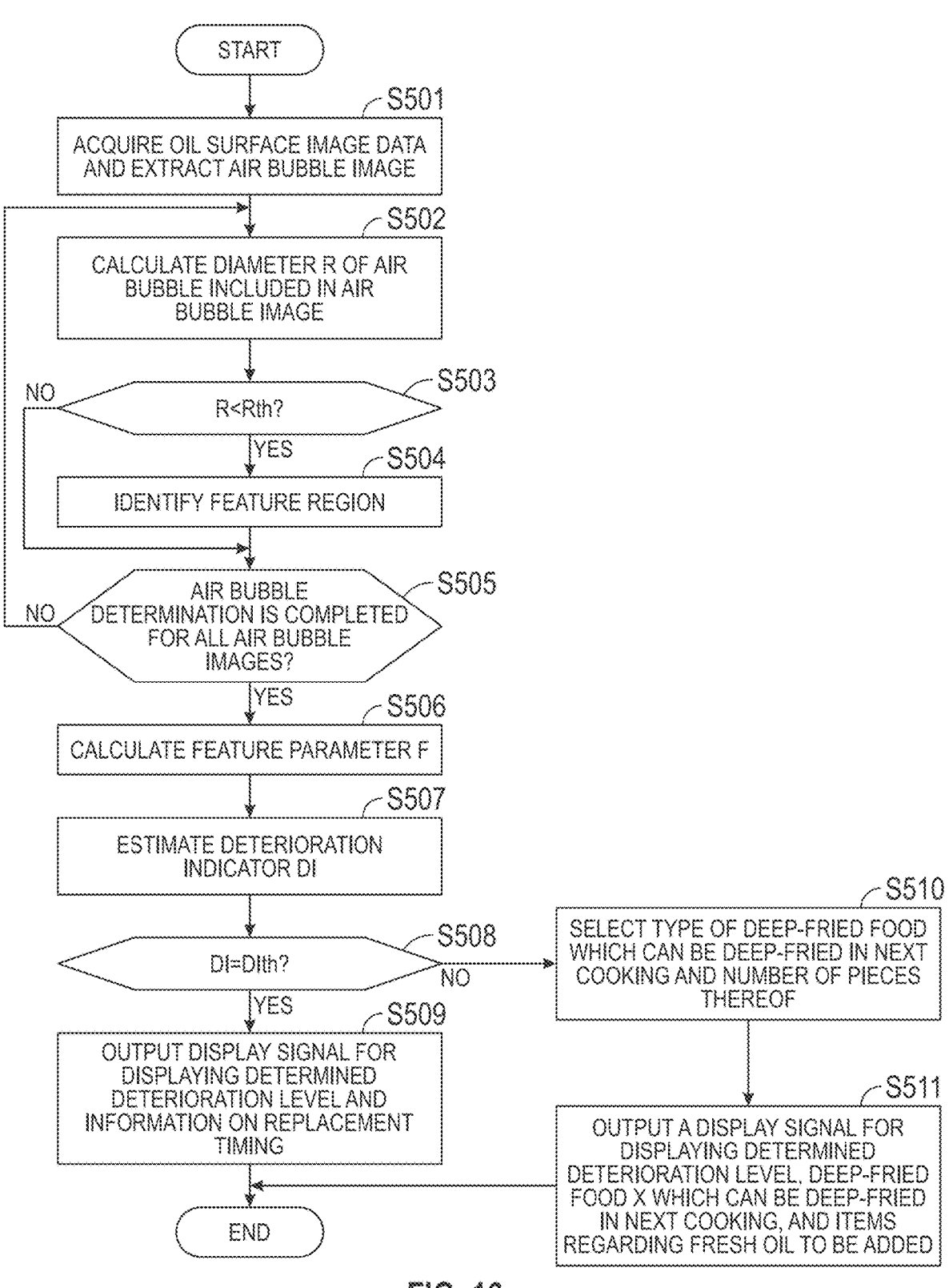
FIG. 16 is a flowchart illustrating a flow of processing executed by a deterioration level determination device.

FIG. 16 is a flowchart illustrating a flow of the processing executed in the deterioration level determination device 5.

Firstly, the oil surface image acquisition section 50 acquires the oil surface image data output from the video camera 42, and the air bubble image extraction section 51 extracts the air bubble images from the oil surface image data (step S501).

Next, the air bubble dimension calculation section 52 calculates the "size R" of all air bubbles included in one of the air bubble images extracted in step S501 (step S502). Subsequently, the feature region identification section 53 determines whether the size R of each air bubble calculated in step S502 is less than the dimension threshold value Rth (step S503).

When it is determined in step S503 that the size R is smaller than the dimension threshold value Rth (R<Rth) and thus each air bubble having the size R is a fine air bubble β (step S503/YES), the feature region identification section 53 identifies, as a feature region, a region including each air bubble, in other words, a region in the air bubble image where the fine air bubbles β are included (step S504). The process of S504 is executed for all the air bubbles included in a specific partial region.

On the other hand, when it is determined in step S503 that the diameter R of each air bubble is equal to or more than the dimension threshold value Rth (R≥Rth) and thus each air bubble is the large air bubble α (step S503/NO), the process of step S504 is not executed.

Subsequently, it is determined whether the processes from step S502 to step S504 have been completed for all the air bubble images extracted in S501 (step S505). If there is an unprocessed air bubble image (step S505/NO), the flow of the processing returns to step S502. In the present embodiment, the deterioration level determination device 5 executes the processes from step S502 to step S505, however, these processes do not necessarily have to be executed. The processes from step S501 to step S506 may be skipped.

When the processes from step S502 to step S504 are completed for all the air bubble images extracted in step S501 (step S505/YES), the feature parameter calculation section 54 calculates the feature parameter F in each feature region identified in step S504 (step S506). In the process of step S506, the feature parameter F is calculated for each element, which has been listed and described above, in each feature region. Thus, the feature parameter F may be calculated as an average value obtained by dividing each element by the number of feature regions.

Then, the deterioration indicator estimation section 55 estimates the deterioration indicator DI based on the feature parameter F calculated in step S506 (step S507). The deterioration indicator estimated in step S507 is calculated, as an estimated value, for each element of the feature parameter F based on the correlation data which have been described above.

Subsequently, the deterioration level determination section 56 compares the deterioration indicator DI estimated in step S507 with the deterioration threshold DIth (step S508).

In step S508, when it is determined that the deterioration indicator DI has the same value as the deterioration threshold value DIth (DI=DIth) (step S508/YES), the replacement timing decision section 57 decides that it is time for changing the frying oil Y, and the notification section 59 outputs, to the monitor 41, a display signal related to the deterioration level (%) determined in step S508 and a display signal informing that it is time for changing the frying oil Y (step S509). Then, the processing in the deterioration level determination device 5 is ended.

In step S508, when it is determined that the deterioration indicator DI has a value different from the deterioration threshold value DIth (DI<DIth) (step S508/NO), the selection section 58 selects the type of the deep-fried food X which can be deep-fried for the next cooking and the number of pieces thereof (step S510). Then, the notification section 59 outputs, to the monitor 41, a display signal related to the deterioration level (%) determined in step S508 and a display signal related to the type of the deep-fried food X selected in step S509 and the number of pieces thereof and the items regarding fresh frying oil to be added based on the selection result in step S509 (step S511). Then, the processing in the deterioration level determination device 5 is ended.

Estimating the deterioration indicator DI by using the feature parameter F calculated based on air bubbles formed on the surface of the frying oil Y after the deep-fried food X is placed therein enables precise determination of the deterioration level of the frying oil Y without depending on the subjectivity of a person who is in charge of determination. Furthermore, in the present embodiment, among the plurality of air bubbles formed on the surface of the frying oil Y, the feature parameter F of the fine air bubbles β which are frequently formed due to the deterioration of the frying oil Y is used to estimate the deterioration indicator DI so as to determine the deterioration level of the frying oil Y. As a result, compared to the case of estimating the deterioration indicator DI by using the feature parameter F of all air bubbles, it is possible to improve the precision of determination.

Second Embodiment

Figure 17:
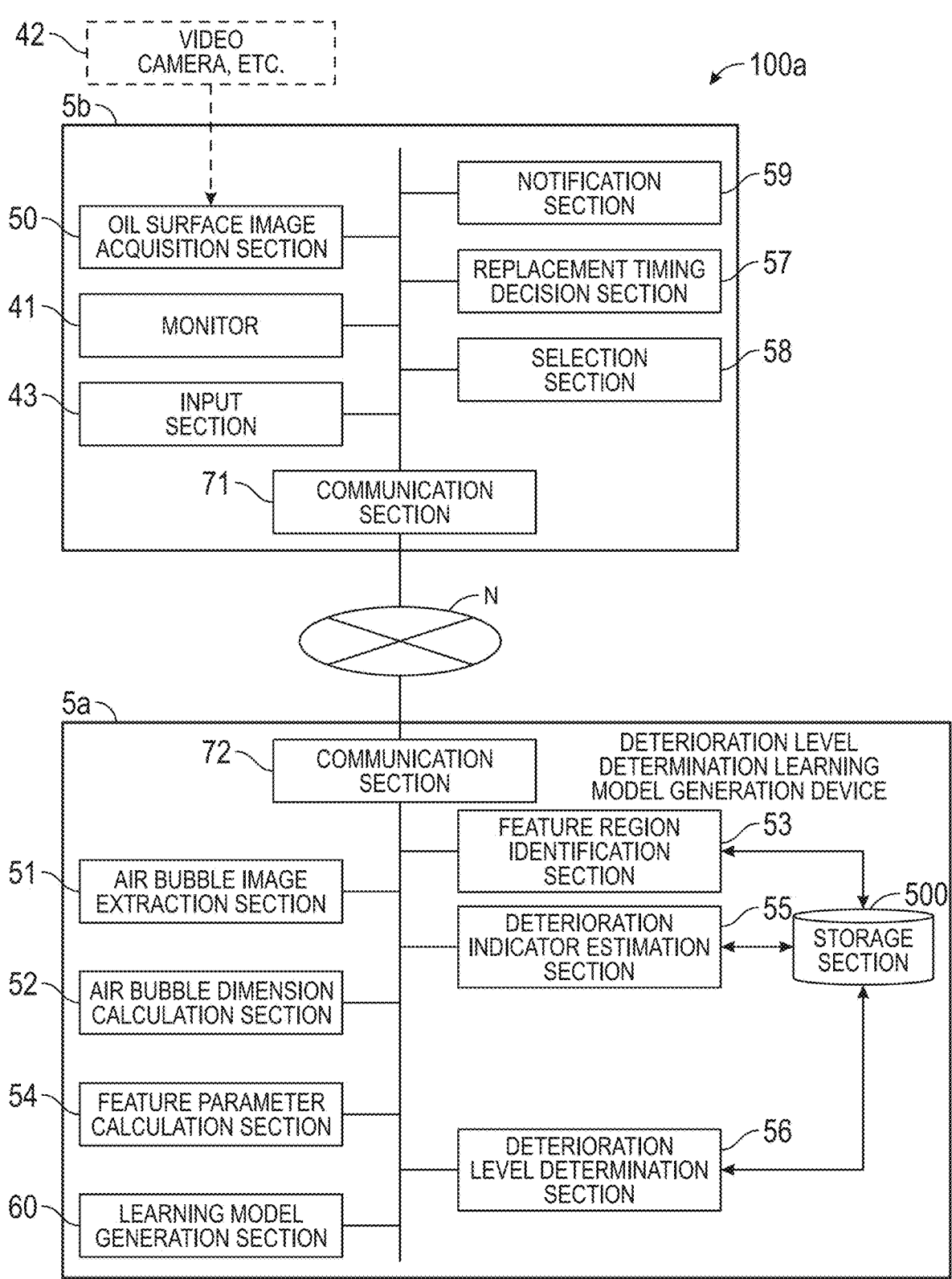
FIG. 17 is a functional block diagram illustrating functions of a deterioration level determination system.

Next, a deterioration level determination system 100a according to a second embodiment of the present invention will be described with reference to FIG. 17. The deterioration level determination system 100a according to the present embodiment includes a deterioration level determination learning model generation device 5a. The deterioration level determination learning model generation device 5a is configured to generate a learning model for determining the deterioration level of frying oil by using data including a plurality of data sets in which oil surface images of the fry basket 3 captured at arbitrary times (timings) while the user is performing deep-fry cooking are associated with various indicators related to determination of the deterioration level of the frying oil in the fry basket 3 at that time.

The terminal device 5b communicatively connected to the deterioration level determination learning model generation device 5a via a communication network N provides an input interface of the oil surface image related to the frying oil.

The various indicators related to the determination of the deterioration level include a plurality of indicators listed and described in the first embodiment. For example, they include information acquired through image processing, such as "the number of air bubbles", "size of each air bubble", "area ratio corresponding to a ratio of the area of a region, where an air bubble having a specific size is present, relative to the total area", and "time from formation of a specific air bubble to disappearance thereof (disappearance speed)". The various indicators further include, for example, "acid value" of frying oil which is an object of imaging at the time of acquiring the oil surface image, "color tone" thereof, "increase rate of viscosity" thereof, "level of stream of air bubbles", "visibility level of the contour of a deep-frying object within an image", the type of frying oil, and the type of a deep-frying object (ingredient to be deep-fried) and the number of pieces thereof.

The deterioration level determination system 100a uses a learning model generated based on the data as exemplified above to update the data in the storage section 500 provided in the deterioration level determination learning model generation device 5a that is communicatively connected to the terminal device 5b used by a user via the communication network N, thereby improving the precision of determination of the deterioration level of the frying oil.

The deterioration level determination learning model generation device 5a may be configured to generate the learning model per user who creates and inputs the data. In this case, when performing the determination of the deterioration level of the frying oil using a learning model, each user uses only the learning model generated based on the data provided by each user themselves. This enables determination of the deterioration specifically to each user's cooking environment (type of frying oil to be used, type of a deep-frying object).

The deterioration level determination learning model generation device 5a may be configured to generate the learning model without distinguishing units of users who create and input data. In this case, the learning model can be generated using a larger amount of data. When the generated learning model is used, the deterioration level of the frying oil is determined using the characteristics (type of frying oil, type of a deep-frying object and the number of pieces thereof), which are predefined per user unit, and the oil surface image as input data. This enables highly precise deterioration determination using a learning model with a larger amount of machine learning based on the cooking environments of a plurality of users (type of frying oil, type of a deep-frying object).

The terminal device 5b includes the same configuration as that of the deterioration level determination device 5 as already described above, that is, the oil surface image acquisition section 50, the replacement timing decision section 57, the selection section 58, and the notification section 59, and further includes a communication section 71. Furthermore, the terminal device 5b includes an input section 43 for inputting data. The input section 43 includes an input device for inputting character information and numerical information by user's manipulation, such as a mouse and a keyboard, and a data reading device for reading a group of data stored in a storage medium.

The terminal device 5b includes the same configuration as that of the deterioration level determination device 5 as already described above, that is, the oil surface image acquisition section 50, the replacement timing decision section 57, the selection section 58, and the notification section 59, and further includes a communication section 71.

Similarly, the deterioration level determination learning model generation device 5a which is one of the aspects of a machine learning device includes the same configuration as that of the deterioration level determination device 5 as already described above, that is, the air bubble image extraction section 51, the air bubble dimension calculation section 52, the feature region identification section 53, the feature parameter calculation section 54, the deterioration indicator estimation section 55, the deterioration level determination section 56, and the storage section 500, and further includes a communication section 72 and a learning model generation section 60.

Each of the communication section 71 and the communication section 72 provides a function including an interface for mutual information communication via the communication network N.

Furthermore, each of the oil surface image acquisition section 50, the air bubble image extraction section 51, the bubble dimension calculation section 52, the feature region identification section 53, the feature parameter calculation section 54, the deterioration indicator estimation section 55, the deterioration level determination section 56, the replacement timing decision section 57, the selection section 58, the notification section 59, and the storage section 500 which has the same configuration as that of the deterioration level determination device 5 provides the same function. These functions are implemented by remotely installed hardware resources, and connecting them in a communicative manner enables implementation of the same functions and processing flows as those of the deterioration level determination device 5.

Based on the feature parameter F calculated by the learning model generation section 60 and the feature parameter calculation section 54, so-called machine learning is executed, and using indicator data (explanatory variables) stored in advance in the storage section 500, for example, a calibration line (model equation) is generated by, for example, linear regression, support vector machine (SVM), bugging, boosting, AdaBoost, decision tree, random forest, logistic regression, neural network, deep learning, in deep learning, especially a convolution neural network (CNN) and recurrent neural network (RNN), long short-term memory (LSTM), or the like.

As the type of linear regression (analysis), for example, single regression, multiple regression, partial least-squares (PLS) regression, and orthogonal projection partial least squares (OPLS: orthogonal partial least squares) regression have been known. At least one of these types can be selected and used.

Single regression is an approach for predicting one objective variable by one explanatory variable while multiple regression is an approach for predicting one objective variable by a plurality of explanatory variables. The (orthogonal projection) partial least squares regression is an approach for extracting principal components corresponding to small features (obtained by principal component analysis with explanatory variables only) so that the covariance between the principal components and the objective variable is maximized. The (orthogonal projection) partial least squares regression is a suitable approach when the number of explanatory variables is greater than the number of samples and the correlation among explanatory variables is strong.

By applying the calibration curve obtained by the machine learning in the learning model generation section 60 to the oil surface image acquired through the oil surface image acquisition section 50, it is possible to estimate the deterioration level of the frying oil Y and thus provide the estimation result.

Third Embodiment

Next, an oil and fat replacement system 200 according to a third embodiment of the present invention will be described with reference to FIG. 18.

Figure 18:
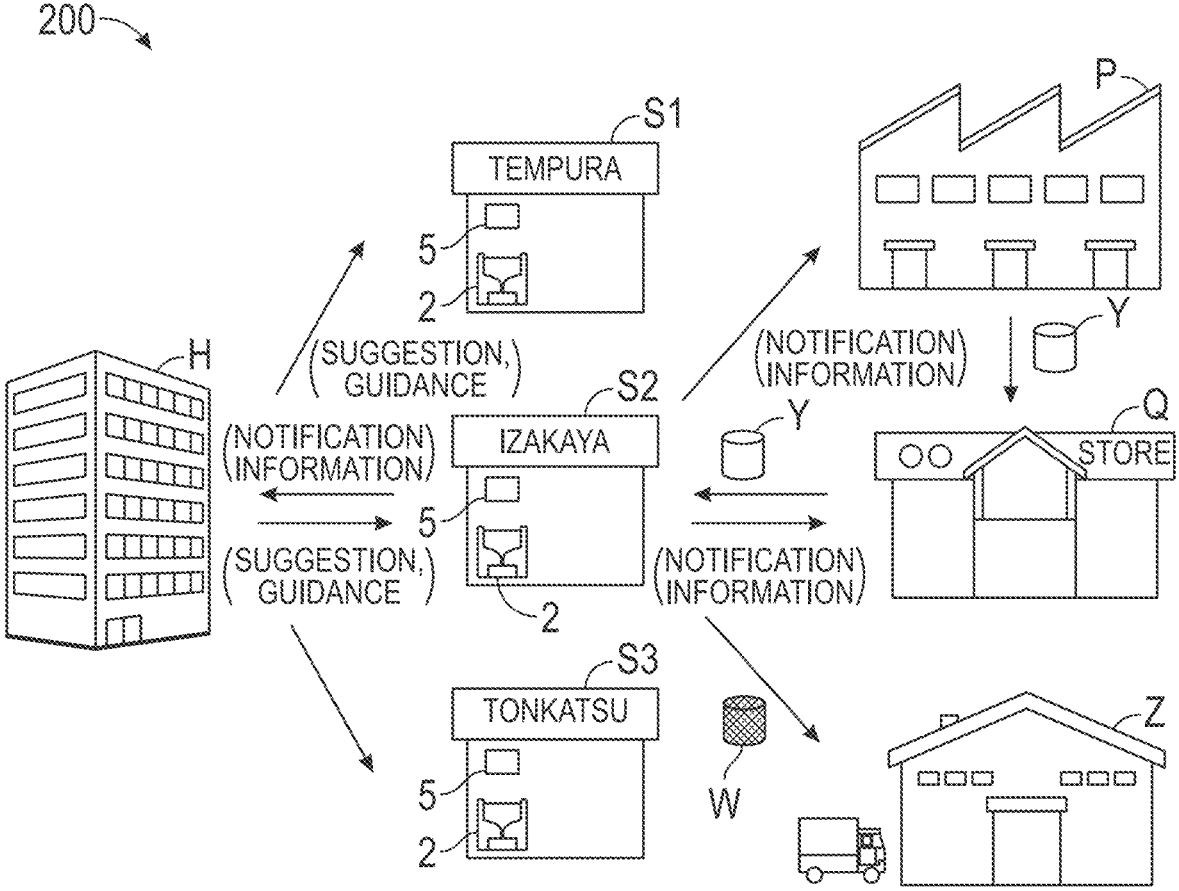
FIG. 18 is a diagram for explaining an oil and fat replacement system.

As illustrated in FIG. 18, the oil and fat replacement system 200 includes shops S1 to S3 each of which is provided with the deterioration level determination device 5 and the fryer 2, a headquarters H for controlling and managing the shops S1 to S3, a manufacturer (oil and fat manufacturer) [[X]] P of frying oil Y used in the shops S1 to S3, a seller (wholesaler or store) [[Y]] Q, and a disposal company Z that collects waste oil W. Since the oil and fat manufacturer X may sell oil directly to customers, the seller Q is a designation that herein includes the oil and fat manufacturer.

In the first embodiment, when it is determined that the deterioration level of the frying oil Y exceeds a predetermined threshold value, the notification section 59 of the deterioration level determination device 5 notifies the user of the information by means of the monitor 41 or the like. In the present embodiment, in addition to such notification, the notification section 59 outputs notification information regarding the deterioration level of the frying oil Y. The notification information may include the content that the deterioration level of the frying oil Y has exceeded the threshold value, or may be a forecast that the deterioration level is about to exceed the threshold value soon.

As illustrated in FIG. 18, upon receiving the notification information from the shop S2 (izakaya), the headquarters H analyzes the number of times that the notification information is received, frequency thereof, and the like. Then, the headquarters H provides suggestions or guidance as to whether the usage of the frying oil is appropriate, the frying oil is appropriately changed, the usage is not wasteful, and the like, not only to the shop S2 but also to the shop S1 (tempura restaurant) and the shop S3 (tonkatsu restaurant) as necessary.

The headquarters H is not limited to a position to manage a plurality of shops and stores, but may manage a plurality of factories provided with fryers. The headquarters H may also manage a plurality of fryers 2 provided in a store or a factory.

The manufacturer P of frying oil and the seller Q of frying oil are also notified of this notification information. Upon receiving the notification information, the manufacturer P forms a manufacturing plan or a sales plan for frying oil. Furthermore, upon receiving the notification information, the seller Q orders and purchases the fresh frying oil Y from the manufacturer P. Then, the seller Q distributes the fresh frying oil Y to the shop S2 (also to the shop S1 and the shop S3 if necessary).

Still further, the disposal company Z (may be the manufacturer P) of the frying oil Y is notified of this notification information. Upon receiving the notification information, the disposal company Z arranges collection of waste oil W. For example, when receiving the notification information for a predetermined number of times, the disposal company Z visits the shop S2 to collect the waste oil W from the oil vat 21 of the fryer 2.

Still further, the notification information may be notified to a cleaning operator (not illustrated). Upon receiving the notification information, the cleaning operator visits the shop S2 to clean the inside of the oil vat 21 of the fryer 2 and therearound. Thus, it is possible to quickly perform a series of operations including supply of frying oil to the shops S1 to S3, disposal of waste oil, and cleaning.

In the case that replacement of the frying oil in the shops and stores is automated based on the content of the notification, it is possible to reduce the burden on a user (employee in the shops and stores). In this case, output of the notification information indicating that the deterioration level of the frying oil exceeds the threshold value automatically triggers the initiation of change of the frying oil.

In the above, the present invention has been described with reference to each of the embodiments of the present invention. The present invention is not limited to each of the embodiments described above, and various modifications may be made therein. For example, each of the embodiments is described in detail herein for the purpose of clarity and a concise description, and the present invention is not necessarily limited to those including all the features described above. Furthermore, some of the features according to a predetermined embodiment can be replaced with other features according to the separate embodiments, and other features can be added to the configuration of a predetermined embodiment. Still further, some of the features can include other features of the separate embodiments, be deleted, and/or replaced.

REFERENCE SIGNS LIST

1: cooking area
2: fryer
3: fry basket
5: deterioration level determination device
5a: deterioration level determination learning model generation device (machine learning device)
5b: terminal device
10A: wall
10B: ceiling
21: oil vat
22: housing
22A: switch
30: handle
41: monitor (notification device)
42: video camera
50: oil surface image acquisition section
51: air bubble image extraction section
52: air bubble dimension calculation section
53: feature region identification section
54: feature parameter calculation section
55: deterioration indicator estimation section
56: deterioration level determination section
57: replacement timing decision section
58: selection section
59: notification section
60: learning model generation section
71: communication section
72: communication section
100: deterioration level determination system
200: oil and fat replacement system
500: storage section

The invention claimed is:

1. An edible oil deterioration level determination device configured for determining a deterioration level of edible oil used for deep-fry cooking performed to cook a deep-fried food, the edible oil deterioration level determination device comprising:

an air bubble image extraction section configured to extract an air bubble image, which is an image of a portion of air bubbles formed due to the deep-fry cooking, from an oil surface image which is an image of a surface of the edible oil during the deep-fry cooking;

a feature parameter calculation section configured to calculate a feature parameter, the feature parameter being a parameter characterizing deterioration of the edible oil, from the air bubble image extracted by the air bubble image extraction section, and the feature parameter including one or more feature parameters selected from an area ratio of the air bubble image relative to a total area of the oil surface image, a cumulative value of the area ratio of the air bubble image relative to the total area of the oil surface image, the number of air bubbles, disappearance speed of air bubbles, presence or absence of a stream of air bubbles, and difference between a color of the edible oil and a color of a region of the deep-fried food;

a deterioration indicator estimation section configured to estimate a deterioration indicator of the edible oil based on the feature parameter calculated by the feature parameter calculation section; and a deterioration level determination section configured to determine the deterioration level of the edible oil based on the deterioration indicator estimated by the deterioration indicator estimation section.

2. The edible oil deterioration level determination device according to claim 1, wherein the deterioration indicator includes one or more deterioration indicators selected from viscosity of the edible oil, a rate of increase in viscosity of the edible oil, acid value (AV) of the edible oil, color tone of the edible oil, anisidine value of the edible oil, quantity of polar compounds of the edible oil, carbonyl value of the edible oil, a smoke point of the edible oil, tocopherol content of the edible oil, iodine value of the edible oil, a refractive index of the edible oil, quantity of volatile compounds of the edible oil, composition of volatile compounds of the edible oil, flavor of the edible oil, quantity of volatile compounds of the deep-fried food obtained by deep-fry cooking with the edible oil, composition of volatile compounds of the deep-fried food obtained by deep-fry cooking with the edible oil, and flavor of the deep-fried food obtained by deep-fry cooking with the edible oil.

3. The edible oil deterioration level determination device according to claim 1, further comprising a notification section configured to output, to a notification device, a notification signal related to the deterioration level of the edible oil determined by the deterioration level determination section.

4. The edible oil deterioration level determination device according to claim 3, further comprising a timing decision section configured to decide whether it is time for replacing the edible oil based on the deterioration level of the edible oil determined by the deterioration level determination section, wherein when the timing decision section decides that it is time for replacing the edible oil, the notification section outputs, to the notification device, a notification signal related to a replacement timing as decided.

5. The edible oil deterioration level determination device according to claim 1, further comprising a selection section configured to select a type of a deep-fried food that can be deep-fried with the edible oil and the number of pieces for each type based on the deterioration level of the edible oil determined by the deterioration level determination section.

6. An edible oil deterioration level determination device configured for determining a deterioration level of edible oil used for deep-fry cooking performed to cook a deep-fried food, the edible oil deterioration level determination device comprising:

an air bubble image extraction section configured to extract an air bubble image, which is an image of a portion of air bubbles formed due to the deep-fry cooking, from an oil surface image which is an image of a surface of the edible oil during the deep-fry cooking;

an air bubble dimension calculation section configured to calculate a size of each of the air bubbles included in the air bubble image extracted by the air bubble image extraction section;

a feature region identification section configured to identify a feature region, which is a region of a predetermined air bubble characterizing deterioration of the edible oil, based on the size of each of the air bubbles calculated by the air bubble dimension calculation section;

a feature parameter calculation section configured to calculate a feature parameter which is a parameter characterizing the deterioration of the edible oil, in the feature region identified by the feature region identification section;

a deterioration indicator estimation section configured to estimate a deterioration indicator of the edible oil based on the feature parameter calculated by the feature parameter calculation section; and a deterioration level determination section configured to determine the deterioration level of the edible oil based on the deterioration indicator estimated by the deterioration indicator estimation section.

7. The edible oil deterioration level determination device according to claim 6, wherein the feature parameter includes one or more feature parameters selected from an area ratio of the air bubble image relative to a total area of the oil surface image, a cumulative value of the area ratio of the air bubble image relative to the total area of the oil surface image, the number of air bubbles, disappearance speed of air bubbles, presence or absence of a stream of air bubbles, and difference between a color of the edible oil and a color of a region of the deep-fried food.

8. The edible oil deterioration level determination device according to claim 6, wherein the deterioration indicator includes one or more deterioration indicators selected from viscosity of the edible oil, a rate of increase in viscosity of the edible oil, acid value (AV) of the edible oil, color tone of the edible oil, anisidine value of the edible oil, quantity of polar compounds of the edible oil, carbonyl value of the edible oil, a smoke point of the edible oil, tocopherol content of the edible oil, iodine value of the edible oil, a refractive index of the edible oil, quantity of volatile compounds of the edible oil, composition of volatile compounds of the edible oil, flavor of the edible oil, quantity of volatile compounds of the deep-fried food obtained by deep-fry cooking with the edible oil, composition of volatile compounds of the deep-fried food obtained by deep-fry cooking with the edible oil, and flavor of the deep-fried food obtained by deep-fry cooking with the edible oil.

9. The edible oil deterioration level determination device according to claim 6, further comprising a notification section configured to output, to a notification device, a notification signal related to the deterioration level of the edible oil determined by the deterioration level determination section.

10. The edible oil deterioration level determination device according to claim 9, further comprising a timing decision section configured to decide whether it is time for replacing the edible oil based on the deterioration level of the edible oil determined by the deterioration level determination section, wherein when the timing decision section decides that it is time for replacing the edible oil, the notification section outputs, to the notification device, a notification signal related to a replacement timing as decided.

11. The edible oil deterioration level determination device according to claim 6, further comprising a selection section configured to select a type of a deep-fried food that can be deep-fried with the edible oil and the number of pieces for each type based on the deterioration level of the edible oil determined by the deterioration level determination section.

* * * * *